US008404723B2

(12) United States Patent
Barfacker et al.

(10) Patent No.: US 8,404,723 B2
(45) Date of Patent: Mar. 26, 2013

(54) 3-CYANO 5-THIAZAHETEROARYL-DIHYDROPYRIDINE AND THE USE THEREOF FOR THE TREATMENT OF CARDIOVASCULAR DISEASES

(75) Inventors: Lars Barfacker, Oberhausen (DE); Peter Kolkhof, Wuppertal (DE); Karl-Heinz Schlemmer, Wuppertal (DE); Rolf Grosser, Leverkusen (DE); Adam Nitsche, Pulheim (DE)

(73) Assignee: Bayer Intellectual Property GmbH, Monheim (DE)

( * ) Notice: Subject to any disclaimer, the term of this patent is extended or adjusted under 35 U.S.C. 154(b) by 437 days.

(21) Appl. No.: 12/442,399

(22) PCT Filed: Sep. 8, 2007

(86) PCT No.: PCT/EP2007/007844
§ 371 (c)(1),
(2), (4) Date: Mar. 21, 2009

(87) PCT Pub. No.: WO2008/034534
PCT Pub. Date: Mar. 27, 2008

(65) Prior Publication Data
US 2010/0240620 A1    Sep. 23, 2010

(30) Foreign Application Priority Data

Sep. 22, 2006 (DE) .......................... 10 2006 044 696

(51) Int. Cl.
*A61K 31/4436* (2006.01)
*C07D 417/04* (2006.01)
(52) U.S. Cl. ..................................... 514/342; 546/270.4
(58) Field of Classification Search ............... 546/270.4; 514/342
See application file for complete search history.

(56) References Cited

U.S. PATENT DOCUMENTS

| 3,635,977 | A | 1/1972 | Lutz |
| 4,558,058 | A | 12/1985 | Schonafinger et al. |
| 4,681,891 | A | 7/1987 | Schonafinger et al. |
| 6,693,102 | B2 | 2/2004 | Stasch et al. |
| 6,743,798 | B1 | 6/2004 | Straub et al. |
| 6,833,364 | B1 | 12/2004 | Straub et al. |
| 6,864,287 | B1 | 3/2005 | Alonso-Alija et al. |
| 7,087,644 | B1 | 8/2006 | Alonso-Alija et al. |
| 7,109,218 | B2 | 9/2006 | Rosentreter et al. |
| 7,135,486 | B1 | 11/2006 | Rosentreter et al. |
| 7,173,037 | B2 | 2/2007 | Alonso-Alija et al. |
| 7,674,825 | B2 | 3/2010 | Alonso-Alija et al. |
| 7,705,043 | B2 | 4/2010 | Alonso-Alija et al. |
| 7,989,633 | B2 | 8/2011 | Kuhl et al. |
| 8,058,447 | B2 | 11/2011 | Kuhl et al. |
| 2004/0176446 | A1 | 9/2004 | Alonso-Alija et al. |
| 2006/0154969 | A1 | 7/2006 | Rosentreter et al. |
| 2008/0269300 | A1 | 10/2008 | Erguden et al. |

FOREIGN PATENT DOCUMENTS

| DE | 3709352 A1 | 9/1988 |
| EP | 0116708 A1 | 8/1984 |
| EP | 0177965 A2 | 4/1986 |
| EP | 0183091 | 6/1986 |
| EP | 0183091 A2 | 6/1986 |
| EP | 1302463 A1 | 4/2003 |
| WO | WO-99/32117 A1 | 7/1999 |
| WO | WO-00/06568 A1 | 2/2000 |
| WO | WO-00/06569 A1 | 2/2000 |
| WO | WO-01/19355 A2 | 3/2001 |
| WO | WO-01/19776 A2 | 3/2001 |
| WO | WO-01/19778 A1 | 3/2001 |
| WO | WO-01/19780 A2 | 3/2001 |
| WO | WO-01/25210 A2 | 4/2001 |
| WO | WO-01/62233 A2 | 8/2001 |
| WO | WO-02/42301 A1 | 5/2002 |
| WO | WO-02/50071 A1 | 6/2002 |
| WO | WO-02/070462 A1 | 9/2002 |
| WO | WO-02/070485 A1 | 9/2002 |
| WO | WO-02/070510 A2 | 9/2002 |
| WO | WO-03/053441 A1 | 7/2003 |
| WO | WO-03/095451 A1 | 11/2003 |
| WO | WO-2004/054505 A2 | 7/2004 |
| WO | WO-2005/046603 A2 | 5/2005 |
| WO | WO-2005/087740 A1 | 9/2005 |
| WO | WO 2005/097118 | 10/2005 |
| WO | WO-2006/027142 A1 | 3/2006 |
| WO | WO-2006/034446 A2 | 3/2006 |
| WO | WO-2006/066011 A2 | 6/2006 |

OTHER PUBLICATIONS

Vippagunta et al., "Crystalline Solid", Advanced Drug Delivery Reviews 48 (2001) 3-26.*
Guillory (In Brittain ed), "Polymorphism in Pharmaceutical Sciences.," NY: Marcel Dekker, Inc., 1999, 1-2, 125-181 and 183-226.*
Mannhold et al., "Calcium- and calmodulin-antagonism of elnadipine derivatives: Comparative SAR", Eur. J. Med. Chem., (1992), 27, pp. 229-235.
English translation of the Abstract of WO 2005/097118.
English translation of the Abstract of EP0183091.
M. E. Olah et al.: "Cloning, Expression, and Characterization of the Unique Bovine $A_1$ Adenosine Receptor," The Journal of Biological Chemistry, vol. 367, No. 15, May 25, 1991, pp. 10764-10770.
K-N. Klotz et al.: "Comparative Pharmacology of Human Adenosine Receptor Subtypes—Characterization of Stably Transfected Receptors in CHO Cells," Naunyn-Schmiedeberg's Arch Pharmacol, 357, 1998, pp. 1-9.
S-A Poulsen et al.: "Adenosine Receptors: New Opportunities for Future Drugs," Bioorganic & Medicinal Chemistry, 6, 1998, pp. 619-641.
R. E. Booth et al.: "Aldosterone," Advances in Physiology Education, vol. 26, No. 1, Mar. 2002, pp. 8-20.
B. Pitt et al.: "Eplerenone, A Selective Aldosterone Blocker, in Patients with Left Ventricular Dysfunction after Myocardial Infarction," The New England Journal of Medicine, vol. 348, No. 14, Apr. 3, 2003, pp. 1309-1321.

(Continued)

*Primary Examiner* — Patricia Morris
(74) *Attorney, Agent, or Firm* — Karen B. King

(57) ABSTRACT

The present application relates to novel aryl-substituted 3-cyano-5-thiazolyl- and 3-cyano-5-thiadiazolyl-1,4-dihydropyridines, a process for their preparation, their use for the treatment and/or prophylaxis of diseases, and their use for the manufacture of medicaments for the treatment and/or prophylaxis of diseases, especially cardiovascular disorders.

5 Claims, No Drawings

OTHER PUBLICATIONS

L. Seiler et al.: "Der Aldosteron-Renin-Quotient bei Sekundarer Hypertonie," Herz, vol. 28, No. 8, 2003, 686-691.

M. A. Zaman et al.; "Drugs Targeting the Renin-Angiotension-Aldosterone System," Nature Reviews Drug Discovery, vol. 1, Aug. 2002, pp. 621-636.

M. Costa et al: "Action of (2-Benzothiazolyl) Methyllithium with Organic Polar Functions," J. Heterocyclic Chem., vol. 28, 1991, pp. 1541-1544.

D. M. Stout et al.: " Recent Advances in the Chemistry of Dihydropyridines," Chem. Rev., vol. 82, 1982, pp. 223-243.

V. F. Bossert et al: "4-Aryldihydropyridine Eine Neue Klasse Hochwirksamer Calcium-Antagonisten," Angew. Chem. vol. 93, 1981, pp. 755-763.

H. Lund: "Quaternization Reactions," Acta Chemica Scandinavica, vol. 27, 1973, pp. 391-395.

T. Watanabe et al.: "Indoles. III. A New Synthesis of 4-Indolecarboxylic Acid," Chem. Pharm. Bull, vol. 20, No. 10, 1972, pp. 2123-2126.

T. Saito et al.: "Synthesis of 1,3,4-Thiadiazol-2-ylacetic Acid Derivatives," J. Heterocyclic Chem., vol. 20, 1983, pp. 73-75.

N. Halland et al.: "Direct Organocatalytic Asymmetric.α-Chlorination of Aldehydes," J. Am. Chem. Soc., vol. 126, 2004, pp. 4790-4791.

M. Poite et al.: "Nouvelles Syntheses dans la Serie des Alcoyl-5 et Dialcoyl-2,5 Thiazoles," Bull. Chem. Soc. Fr. , 1962, pp. 2078-2085.

C. G. Krespan: "Fluorinated Imines and Hydrazones," J. Org. Chem., vol. 34, 1969, pp. 42-45.

F. J. Ehlert et al.: "The Binding of [$^3$H]Nitrendipine to Receptors for Calcium Channel Antagonists in the Heart, Cerebral Cortex and Ileum of Rats," Life Sciences, vol. 20, 1982, pp. 2191-2202.

H. Meyer et al.: "Dihydropyridniie, II—Synthese von 1,4-Dihydropyridinen mit Bruckenkppf-N-Atom," Liebigs Ann. Chem., 1977, pp. 1888-1894.

H. Meyer et al.: "Synthese von 2-Aminodihydropyridinen durch Michael-Addition," Liebigs Ann. Chem., 1977, pp. 1985-1908.

H. Meyer et al.: :Synthese von 6-Alkoxy-2-Amino-4,5-Dihydropyridin-3,5-Dicarbon-Saureestern, Liebigs Ann. Chem., 1976, pp. 1762-1766.

R. J. Gould et al.: "[$^3$H]Nitrendipine-Labeled Calcium Channels Discriminate Inorganic Calcium Agonists and Antagonists," Proc. Natl. Acad. Sci., vol. 79, Jun. 1982, pp. 3656-3660.

Booth, et al.:"Aldosterone," Adv. Physiol. Educ., 2002, 26(1):8-20.

Funder, "Mineralcorticoid Receptors and Cardiovascular Damage: It's Not Just Aldosterone," Hypertension, 2006, 47:634-635.

Hayashi, et al.:"Immediate Administration of Mineralocorticoid Receptor Antagonist Spironolactone Prevents Post-Infarct Left Ventricular Remodeling Associated With Suppression of a Marker of Myocardial Collagen Synthesis in Patients With First Anterior Acute Myocardial Infarction," Circulation, May 2003, 107(20):2559-2565.

Pitt, et al.:"Eplerenone, a Selective Aldosterone Blocker, in Patients with Left Ventricular Dysfunction after Myocardial Infarction," The New England Journal of Medicine, Apr. 3, 2003, 348(14): 1309-1321.

Pitt, et al.:"The Effect of Spironalactone on Morbidity and Mortality in Patients with Severe Heart Failure," The New England Journal of Medicine, Sep. 2, 1999, 341(10):709-717.

Pitt, et al.:"Neurohumoral Effects of Aliskiren in Patients with Symptomatic Heart Failure Receiving a Mineralocorticoid Receptor Antagonist: The Aliskiren Observation of Heart FailureTreatment study," European Journal of Heart Failure, 2011, 13(7): 755-764.

Rocha, et al.:"Rationale for the Use of Aldosterone Antagonists in Congestive Heart Failure," Drugs, 2002, 62 (5):723-731.

Schmidt, et al.:"Cardioprotective Effects of Mineralocorticoid Receptor Antagonists at Reperfusion," European Heart Journam, 2010, 31:1655-1662.

Seiler, et al,:"Der Aldosteron-Renin-Quotient bei Sekundarer Hypertonie," Herz, 2003, 28(8):686-691.

Takeda:"Pleiotropic Actions of Aldosterone and the Effects of Eplerenone, a Selective Mineralocorticoid Receptor Antagonist," Hypertens. Res., 2004, 27(11):781-789.

Weihong, "Sterioid Receptor Heterodimerization Demonstrated in vitro and in vivo," Proc Natl. Acad. Sci USA, Dec. 1995, 92:12480-12484.

West, Anthony R.:"Solid State Chemistry and its Applications," Wiley, New York, 1988, pp. 358 & 365.

Zaman, et al.:"Drugs Targeting the Renin-Angiotensin-Aldosterone System," Nature Reviews Drug Discovery, Aug. 2002, 1:621-636.

Zannad, et al.:"Effect of MR Blockade on Collagen Formation and Cardiovascular Disease with a Specific Emphasis on Heart Failure," Heart Failure Reviews, 2005, 10:71-78.

* cited by examiner

3-CYANO 5-THIAZAHETEROARYL-DIHYDROPYRIDINE AND THE USE THEREOF FOR THE TREATMENT OF CARDIOVASCULAR DISEASES

RELATED APPLICATIONS/PATENTS AND INCORPORATION BY REFERENCE

This application is a National Stage Application filed under 35 U.S.C. §371 based on International Application No. PCT/EP2007/007844, filed Sep. 8, 2007, which claims priority to German Patent Application Number 102006044696.8, filed Sep. 22, 2006, the entire contents each of which are incorporated herein by reference.

The foregoing applications, and all documents cited therein and all documents cited or referenced therein, and all documents cited or referenced herein, including any U.S. or foreign patents or published patent applications, International patent applications, as well as, any non-patent literature references and any manufacturer's instructions, are hereby expressly incorporated herein by reference.

The present application relates to novel aryl-substituted 3-cyano-5-thiazolyl- and 3-cyano-5-thiadiazolyl-1,4-dihydropyridines, a process for their preparation, their use for the treatment and/or prophylaxis of diseases, and their use for the manufacture of medicaments for the treatment and/or prophylaxis of diseases, especially cardiovascular disorders.

Aldosterone plays a key part in maintaining fluid and electrolyte homeostasis by promoting, in the epithelium of the distal nephron, sodium retention and potassium secretion, thus contributing to keeping the extracellular volume constant and thus to regulating blood pressure. Besides this, aldosterone displays direct effects on the structure and function of the cardiac and vascular system, but the underlying mechanisms thereof are not yet fully explained [R. E. Booth, J. P. Johnson, J. D. Stockand, *Adv. Physiol. Educ.* 26 (1), 8-20 (2002)].

Aldosterone is a steroid hormone which is formed in the adrenal cortex. Its production is regulated indirectly very substantially depending on the renal blood flow. Any decrease in renal blood flow leads to release in the kidney of the enzyme renin into the circulating blood. This in turn activates the formation of angiotensin II, which on the one hand has a constricting effect on the arterial blood vessels, but on the other hand also stimulates the formation of aldosterone in the adrenal cortex. Thus, the kidney acts as blood pressure sensor, and thus indirect volume sensor, in the circulating blood and counteracts, via the renin-angiotensin-aldosterone system, critical losses of volume by on the one hand increasing the blood pressure (angiotensin II effect), and on the other hand, by rebalancing the state of filling of the vascular system by increased reabsorption of sodium and water in the kidney (aldosterone effect).

This control system may be pathologically impaired in diverse ways. Thus, a chronic reduction in renal blood flow (e.g. as a result of heart failure and the congestion of blood in the venous system caused thereby) leads to a chronically excessive release of aldosterone. In turn this is followed by an expansion of the blood volume and thereby increases the weakness of the heart through an excessive supply of volume to the heart. Congestion of blood in the lungs with shortness of breath and formation of edema in the extremities, and ascites and pleural effusions may be the result; the renal blood flow falls further. In addition, the excessive aldosterone effect leads to a reduction in the potassium concentration in the blood and in the extracellular fluid. In heart muscles which have been previously damaged otherwise, cardiac arrhythmias with a fatal outcome may be induced if there is a deviation below a critical minimum level. This is likely to be one of the main causes of the sudden cardiac death which frequently occurs in patients with heart failure.

In addition, aldosterone is also thought to be responsible for a number of the myocardial remodeling processes typically to be observed in heart failure. Thus, hyperaldosteronism is a crucial component in the pathogenesis and prognosis of heart failure which may originally be induced by various types of damage such as, for example, a myocardial infarction, a myocardial inflammation or high blood pressure. This assumption is supported by the fact that there was a marked reduction in overall mortality in wide-ranging clinical studies on groups of patients with chronic heart failure and post acute myocardial infarction through the use of aldosterone antagonists [B. Pitt, F. Zannad, W. J. Remme et al., *N. Engl. J. Med.* 341, 709-717 (1999); B. Pitt, W. Remme, F. Zannad et al., *N. Engl. J. Med.* 348, 1309-1321 (2003)]. It was possible to achieve this inter alia by reducing the incidence of sudden cardiac death.

According to recent studies, a not inconsiderable number of patients suffering from essential hypertension are also found to have a so-called normokalemic variant of primary hyperaldosteronism [prevalence up to 11% of all hypertensives: L. Seiler and M. Reincke, *Der Aldosteron-Renin-Quotient bei sekundärer Hypertonie*, Herz 28, 686-691 (2003)]. The best diagnostic method for normokalemic hyperaldosteronism is the aldosterone/renin quotient of the corresponding plasma concentrations, so that relative elevations in aldosterone in relation to the renin plasma concentrations can also be diagnosed and eventually treated. For this reason, a hyperaldosteronism diagnosed in connection with essential hypertension is a starting point for a causal and prophylactically worthwhile therapy.

Far less common than the types of hyperaldosteronism detailed above are pathological states in which the impairment either is to be found in the hormone-producing cells of the adrenal itself, or the number or mass thereof is increased through hyperplasia or proliferation. Adenomas or diffuse hyperplasias of the adrenal cortex are the commonest cause of the primary hyperaldosteronism referred to as Conn's syndrome, the leading symptoms of which are hypertension and hypokalemic alkalosis. The priority here too, besides surgical removal of the diseased tissue, is medical therapy with aldosterone antagonists [H. A. Kühn and J. Schirmeister (Editors), *Innere Medizin,* 4th edition, Springer Verlag, Berlin, 1982].

Another pathological state associated typically with an elevation of the plasma aldosterone concentration is advanced cirrhosis of the liver. The cause of the aldosterone elevation in this case is mainly the restricted aldosterone breakdown resulting from the impairment of liver function. Volume overload, edema and hypokalemia are the typical consequences, which can be successfully alleviated in clinical practice by aldosterone antagonists.

The effects of aldosterone are mediated by the mineralocorticoid receptor which has an intracellular location in the target cells. The aldosterone antagonists available to date have, like aldosterone itself, a basic steroid structure. The utility of such steroidal antagonists is limited by their interactions with the receptors of other steroid hormones, which in some cases lead to considerable side effects such as gynecomastia and impotence and to discontinuation of the therapy [M. A. Zaman, S. Oparil, D. A. Calhoun, *Nature Rev. Drug Disc.* 1, 621-636 (2002)].

The use of potent, non-steroidal antagonists which are more selective for the mineralocorticoid receptor provides the possibility of avoiding this profile of side effects and thus achieving a distinct therapeutic advantage.

The object of the present invention is to provide novel compounds which can be used as selective mineralocorticoid receptor antagonists for the treatment of disorders, especially cardiovascular disorders.

4-Fluorenonyl-1,4-dihydropyridine derivatives as mineralocorticoid receptor antagonists are disclosed in WO 2005/087740. WO 2005/097118 claims compounds having a 4-aryl-1,4-dihydro-pyridine core structure as aldosterone receptor antagonists. 4-Aryl-3-cyano-1,4-dihydropyridine-5-carboxylic esters and -carboxamides are described in WO 2006/066011 as in some cases dual modulators of steroid hormone receptors and of the L-type calcium channel. EP 0 116 708-A1, EP 0 177 965-A2, EP 0 183 091-A2 and DE 3 709 352-A1 claim inter alia thiazolyl- and thiadiazolyl-substituted 1,4-dihydropyridines as calcium antagonists or agonists for the treatment of cardiovascular disorders. Structure-activity relations of various 5-heteroaryl-1,4-dihydropyridine-3-carboxylic esters are reported in R. Mannhold et al., Eur. J. Med. Chem. 27, 229-235 (1992).

The present invention relates to compounds of the general formula (I)

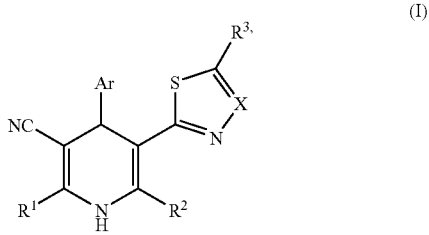

(I)

in which

Ar is $(C_6-C_{10})$-aryl or 5- to 10-membered heteroaryl having up to two ring heteroatoms from the series N, O and/or S, each of which may be substituted once to three times, identically or differently, by substituents selected from the series halogen, cyano, $(C_1-C_4)$-alkyl, $(C_1-C_4)$-alkoxy and $(C_1-C_4)$-alkylthio, where said alkyl, alkoxy and alkylthio radicals may in turn be substituted by cyano or up to three times by fluorine, or Ar is a group of the formula

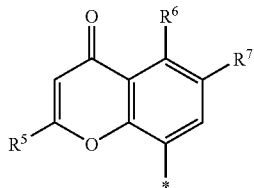

in which

* is the point of linkage to the dihydropyridine ring,
$R^5$ is hydrogen or $(C_1-C_4)$-alkyl,
$R^6$ is hydrogen, fluorine, chlorine, cyano, nitro, trifluoromethyl or $(C_1-C_4)$-alkyl,
and
$R^7$ is hydrogen or fluorine,
$R^1$ is $(C_1-C_6)$-alkyl which may be substituted by phenyl, or is $(C_1-C_6)$-alkylthio, where said alkyl and alkylthio radicals may in turn be substituted up to three times by fluorine, $R^2$ is $(C_1-C_6)$-alkyl which may be substituted by cyano, hydroxy, $(C_1-C_4)$-alkoxy, trifluoromethoxy, amino, mono-$(C_1-C_4)$-alkylamino, di-$(C_1-C_4)$-alkylamino, $(C_3-C_6)$-cycloalkyl, phenyl or up to three times by fluorine, or is $(C_3-C_6)$-cycloalkyl, X is N or C—$R^4$, and $R^3$ and $R^4$ are identical or different and independently of one another are hydrogen, halogen, amino, mono-$(C_1-C_4)$-alkylamino or di-$(C_1-C_4)$-alkylamino, are $(C_1-C_4)$-alkyl which may be substituted by hydroxy, $(C_1-C_4)$-alkoxy, amino, mono-$(C_1-C_4)$-alkylamino, di-$(C_1-C_4)$-alkylamino or up to three times by fluorine, or are phenyl which may be substituted by halogen, cyano, trifluoromethyl, $(C_1-C_4)$-alkoxy or trifluoromethoxy, or $R^3$ and $R^4$, if the latter is present, are linked together and form, together with the carbon atoms to which they are bonded, a fused 5- to 7-membered cycloalkyl ring which may be substituted by $(C_1-C_4)$-alkyl or $(C_1-C_4)$-alkoxy, and in which one ring $CH_2$ group may be replaced by an O atom, or a fused phenyl or pyridyl ring, each of which may be substituted by halogen, cyano, trifluoromethyl, $(C_1-C_4)$-alkoxy or trifluoromethoxy, and the salts, solvates and solvates of the salts thereof.

Compounds of the invention are the compounds of the formula (I) and the salts, solvates and solvates of the salts thereof, the compounds which are encompassed by formula (I) and are of the formulae mentioned hereinafter, and the salts, solvates and solvates of the salts thereof, and the compounds which are encompassed by formula (I) and are mentioned hereinafter as exemplary embodiments, and the salts, solvates and solvates of the salts thereof, insofar as the compounds encompassed by formula (I) and mentioned hereinafter are not already salts, solvates and solvates of the salts.

The compounds of the invention may, depending on their structure, exist in stereoisomeric forms (enantiomers, diastereomers). The invention therefore relates to the enantiomers or diastereomers and respective mixtures thereof The stereoisomerically pure constituents can be isolated in a known manner from such mixtures of enantiomers and/or diastereomers.

If the compounds of the invention may occur in tautomeric forms, the present invention encompasses all tautomeric forms.

Salts which are preferred for the purposes of the present invention are physiologically acceptable salts of the compounds of the invention. Also encompassed are salts which are themselves unsuitable for pharmaceutical uses but can be used for example for isolating or purifying the compounds of the invention.

Physiologically acceptable salts of the compounds of the invention include acid addition salts of mineral acids, carboxylic acids and sulfonic acids, e.g. salts of hydrochloric acid, hydrobromic acid, sulfuric acid, phosphoric acid, methanesulfonic acid, ethanesulfonic acid, toluenesulfonic acid, benzenesulfonic acid, naphthalenedisulfonic acid, acetic acid, trifluoroacetic acid, propionic acid, lactic acid, tartaric acid, malic acid, citric acid, fumaric acid, maleic acid and benzoic acid.

Physiologically acceptable salts of the compounds of the invention include salts of conventional bases such as, by way of example and preferably, alkali metal salts (e.g. sodium and potassium salts), alkaline earth metal salts (e.g. calcium and magnesium salts) and ammonium salts derived from ammonia or organic amines having 1 to 16 C atoms, such as, by way of example and preferably, ethylamine, diethylamine, triethylamine, ethyldiisopropylamine, monoethanolamine, diethanolamine, triethanolamine, dicyclohexylamine, dimethylaminoethanol, procaine, dibenzylamine, N-methylmorpholine, arginine, lysine, ethylenediamine and N-methylpiperidine.

Solvates refers for the purposes of the invention to those forms of the compounds of the invention which form, in the solid or liquid state, a complex by coordination with solvent molecules. Hydrates are a specific form of solvates in which the coordination takes place with water. Hydrates are preferred solvates in the context of the present invention.

The present invention additionally encompasses prodrugs of the compounds of the invention. The term "prodrugs" encompasses compounds which themselves may be biologically active or inactive, but are converted during their residence time in the body into compounds of the invention (for example by metabolism or hydrolysis).

In the context of the present invention, the substituents have the following meaning, unless specified otherwise:

$(C_1-C_6)$-Alkyl and $(C_1-C_4)$-alkyl represent in the context of the invention a straight-chain or branched alkyl radical having respectively 1 to 6 and 1 to 4 carbon atoms. A straight-chain or branched alkyl radical having 1 to 4 carbon atoms is preferred. Mention may be made by way of example and preferably of: methyl, ethyl, n-propyl, isopropyl, n-butyl, isobutyl, sec-butyl, tert-butyl, 1-ethylpropyl, n-pentyl, isopentyl and n-hexyl.

$(C_3-C_6)$-Cycloalkyl represents in the context of the invention a saturated monocyclic carbocycle having 3 to 6 carbon atoms. Mention may be made by way of example and preferably of: cyclopropyl, cyclobutyl, cyclopentyl and cyclohexyl.

A fused 5- to 7-membered cycloalkyl ring represents in the context of the present invention a carbocycle which is saturated apart from the double bond of the fusing position and has 5 to 7 ring atoms.

$(C_1-C_4)$-Alkoxy represents in the context of the invention a straight-chain or branched alkoxy radical having 1 to 4 carbon atoms. Mention may be made by way of example and preferably of: methoxy, ethoxy, n-propoxy, isopropoxy, n-butoxy and tert-butoxy.

$(C_1-C_6)$-Alkylthio and $(C_1-C_4)$-alkylthio represent in the context of the invention a straight-chain or branched alkylthio radical having respectively 1 to 6 and 1 to 4 carbon atoms. A straight-chain or branched alkylthio radical having 1 to 4 carbon atoms is preferred. Mention may be made by way of example and preferably of: methylthio, ethylthio, n-propylthio, isopropylthio, n-butylthio, tert-butylthio, n-pentylthio and n-hexylthio.

Mono-$(C_1-C_4)$-alkylamino represents in the context of the invention an amino group having one straight-chain or branched alkyl substituent which has 1 to 4 carbon atoms. Mention may be made by way of example and preferably of: methylamino, ethylamino, n-propylamino, isopropylamino, n-butylamino and tert-butylamino.

Di-$(C_1-C_4)$-alkylamino represents in the context of the invention an amino group having two identical or different straight-chain or branched alkyl substituents, each of which have 1 to 4 carbon atoms. Mention may be made by way of example and preferably of: N,N-dimethylamino, N,N-diethylamino, N-ethyl-N-methylamino, N-methyl-N-n-propylamino, N-isopropyl-N-n-propylamino, N,N-diisopropylamino, N-n-butyl-N-methylamino and N-tert-butyl-N-methylamino.

$(C_6-C_{10})$-Aryl represents in the context of the invention an aromatic carbocycle having 6 or 10 ring carbon atoms. Preferred aryl radicals are phenyl and naphthyl.

5- to 10-membered heteroaryl represents in the context of the invention a mono- or optionally bicyclic aromatic heterocycle (heteroaromatic) having a total of 5 to 10 ring atoms which comprises up to two identical or different ring heteroatoms from the series N, O and/or S and is linked via a ring carbon atom or, where appropriate, via a ring nitrogen atom. Examples which may be mentioned are: furyl, pyrrolyl, thienyl, pyrazolyl, imidazolyl, thiazolyl, oxazolyl, isoxazolyl, iso-thiazolyl, pyridyl, pyrimidinyl, pyridazinyl, pyrazinyl, benzofuranyl, benzothienyl, benzimidazolyl, benzoxazolyl, benzothiazolyl, indolyl, indazolyl, quinolinyl, isoquinolinyl, naphthyridinyl, quinazolinyl, quinoxalinyl, phthalazinyl. Monocyclic 5- or 6-membered heteroaryl radicals having up to two ring heteroatoms from the series N, O and/or S are preferred, such as, for example, furyl, thienyl, thiazolyl, oxazolyl, isothiazolyl, isoxazolyl, pyrazolyl, imidazolyl, pyridyl, primidinyl, pyridazinyl, pyrazinyl.

Halogen includes in the context of the invention fluorine, chlorine, bromine and iodine. Fluorine, chlorine or bromine are preferred.

If radicals in the compounds of the invention are substituted, the radicals may be substituted one or more times, unless specified otherwise. In the context of the present invention, all radicals which occur more than once have a mutually independent meaning. Substitution by one, two or three identical or different substituents is preferred. Substitution by one substituent is very particularly preferred.

Preference is given to compounds of the formula (I) in which
Ar is a group of the formula

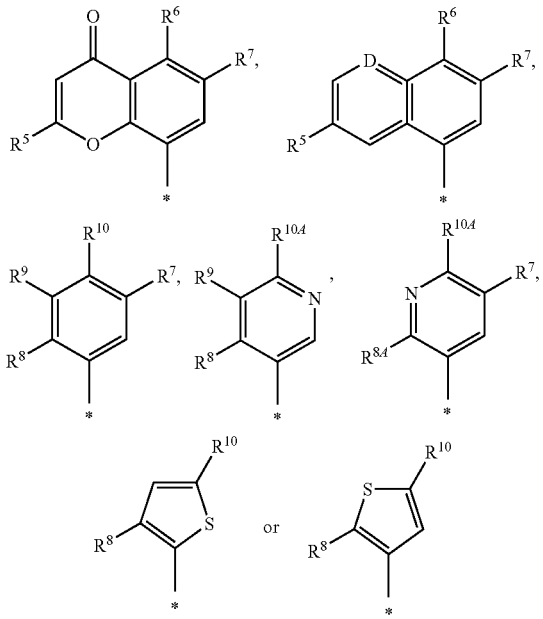

in which
* is the point of linkage to the dihydropyridine ring,
D is N or CH,
$R^5$ is hydrogen, methyl or ethyl,
$R^6$ is hydrogen, fluorine, chlorine or cyano,
$R^7$ is hydrogen or fluorine, $R^8$ is fluorine, chlorine, bromine, cyano or $(C_1-C_4)$-alkyl, $(C_1-C_4)$-alkoxy or $(C_1-C_4)$-alkylthio, each of which may be substituted up to three times by fluorine, $R^{8A}$ is cyano or $(C_1-C_4)$-alkyl, $(C_1-C_4)$-alkoxy or $(C_1-C_4)$-alkylthio, each of which may be substituted up to three times by fluorine, $R^9$ is hydrogen, fluorine, chlorine or methyl, $R^{10}$ is hydrogen, cyano, fluorine, chlorine or bromine, and $R^{10A}$ is hydrogen or cyano, $R^1$ is $(C_1-C_4)$-alkyl which may be substituted up to three times by fluorine, $R^2$ is $(C_1-C_4)$-alkyl which may be substituted by $(C_1-C_4)$-alkoxy or up to three times by fluorine, X is N or C—$R^4$, and $R^3$ and $R^4$ are identical or different and independently of one another are hydrogen, fluorine, chlorine, amino, mono-$(C_1-C_4)$-alkylamino, di-$(C_1-C_4)$-alkylamino or $(C_1-C_4)$-alkyl, or $R^3$ and $R^4$, if the latter is present, are linked together and form, together with the thiazole ring to which they are bonded, a group of the formula in which
# is the point of linkage to the dihdyropyridine ring,
$R^{11}$ is hydrogen, $(C_1-C_4)$-alkyl or $(C_1-C_4)$-alkoxy,
and
$R_{12}$ is hydrogen, fluorine, chlorine, bromine, $(C_1-C_4)$-alkyl, trifluoromethyl, $(C_1-C_4)$-alkoxy or trifluoromethoxy, and the salts, solvates and solvates of the salts thereof.

Particular preference is given to compounds of the formula (I) in which
Ar is a group of the formula in which
* is the point of linkage to the dihydropyridine ring,
$R^8$ is fluorine, chlorine, bromine, cyano, methyl, ethyl, trifluoromethyl, methoxy or trifluoromethoxy,
and
$R^{10}$ is fluorine, chlorine or cyano,
$R^1$ is methyl or trifluoromethyl, $R^2$ is methyl, ethyl, n-propyl or methoxymethyl,
X is C—$R^4$,
$R^3$ is hydrogen, methyl or ethyl,
$R^4$ is hydrogen, methyl, ethyl or n-propyl,
or
$R^3$ and $R^4$ are linked together and form, together with the thiazole ring to which they are bonded, a group of the formula in which
# is the point of linkage to the dihydropyridine ring,
and the salts, solvates and solvates of the salts thereof.

The definitions of radicals indicated specifically in their respective combinations or preferred combinations of radicals are replaced as desired irrespective of the particular combinations indicated for the radicals also by definitions of radicals of other combinations.

Combinations of two or more of the abovementioned preferred ranges are very particularly preferred.

The invention further relates to a process for preparing the compounds of the invention of the formula (I), characterized in that a compound of the formula (II)

$$\text{(II)}$$

in which Ar has the meaning indicated above,
is either
[A] reacted in a one-stage process (one-pot reaction) with a compound of the formula (III)

$$\text{(III)}$$

in which $R^1$ has the meaning indicated above,
and
$M^+$ is an alkali metal ion such as $Li^+$, $Na^+$ or $K^+$,
and a compound of the formula (IV)

$$\text{(IV)}$$

in which $R^2$, $R^3$ and X each have the meanings indicated above, or

[B] reacted in a one-stage process (one-pot reaction) with a compound of the formula (V)

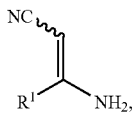
(V)

in which R¹ has the meanings indicated above,
and a compound of the formula (VI)

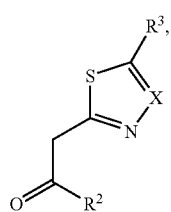
(VI)

in which R², R³ and X each have the meanings indicated above, or

[C] in a two-stage process firstly converted with a compound of the formula (VI) into a compound of the formula (VII)

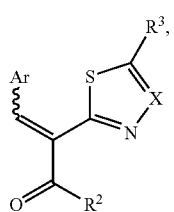
(VII)

in which Ar, R², R³ and X each have the meanings indicated above, and the latter is then reacted in a second step with a compound of the formula (V), and where appropriate the resulting compounds of the formula (I) are separated by methods known to the skilled worker into their enantiomers and/or diastereomers, and/or converted with the appropriate (i) solvents and/or (ii) bases or acids into the solvates, salts and/or solvates of the salts thereof.

The reactions in processes [A], [B] and [C] generally take place in inert solvents, where appropriate in the presence of an acid and/or base, in a temperature range from +20° C. to the boiling point of the solvent under atmospheric pressure.

Inert solvents for processes [A] and [B], and the second stage of process [C], are for example alcohols such as methanol, ethanol, n-propanol, isopropanol, n-butanol or tert-butanol, or other solvents such as acetonitrile, tetrahydrofuran, dioxane, 1,2-dimethoxyethane, toluene or glacial acetic acid. The reactions are preferably carried out in ethanol or isopropanol at the respective reflux temperature under atmospheric pressure.

The reaction in process [A] is preferably carried out in the presence of an acid such as, for example, acetic acid, trifluoroacetic acid, p-toluenesulfonic acid, methanesulfonic acid or tetrabutylammonium bisulfate; the addition of acetic acid is particularly preferred.

The reactions in process [B], and in the second stage of process [C], can be carried out where appropriate advantageously with addition of a base. Examples suitable for this purpose are alkali metal or alkaline earth metal carbonates such as sodium, potassium or cesium carbonate, or alcoholates such as sodium or potassium methanolate, sodium or potassium ethanolate or sodium or potassium tert-butoxide. Potassium tert-butoxide is preferably used.

Inert solvents for the first stage of process [C] are for example halohydrocarbons such as dichloromethane, trichloromethane, tetrachloromethane, trichloroethane or 1,2-dichloroethane, or other solvents such as acetonitrile, pyridine, benzene, toluene, xylene, chlorobenzene, hexane or cyclohexane. The reactions preferably take place in dichloromethane or toluene at the respective reflux temperature under atmospheric pressure.

The reaction in the first stage of process [C] is preferably carried out in the presence of an acid in combination with piperidine or pyridine as base and/or a dehydrating agent such as, for example, molecular sieves. Examples of suitable acids are acetic acid or p-toluenesulfonic acid. A reaction with addition of piperidinium acetate is particularly preferred [see also reaction scheme 11 below; concerning the synthesis of 1,4-dihydropyridines in general, cf. also D. M. Stout, A. I. Meyers, *Chem. Rev.* 1982, 82, 223-243; H. Meier et al., *Liebigs Ann. Chem.* 1977, 1888; H. Meier et al., ibid. 1977, 1895; H. Meier et al., ibid. 1976, 1762; F. Bossert et al., *Angew. Chem.* 1981, 93, 755].

The compounds of the formula (II) are commercially available, disclosed in the literature or can be prepared in analogy to processes disclosed in the literature (cf. reaction schemes 1-7 below). The compounds of the formulae (III), (IV), (V) and (VI) are commercially available, disclosed in the literature or can be prepared by methods disclosed in the literature [concerning the compounds of the formula (VI), cf. also reaction schemes 8-10 below].

The preparation of the compounds of the invention can be illustrated by the following synthesis schemes:

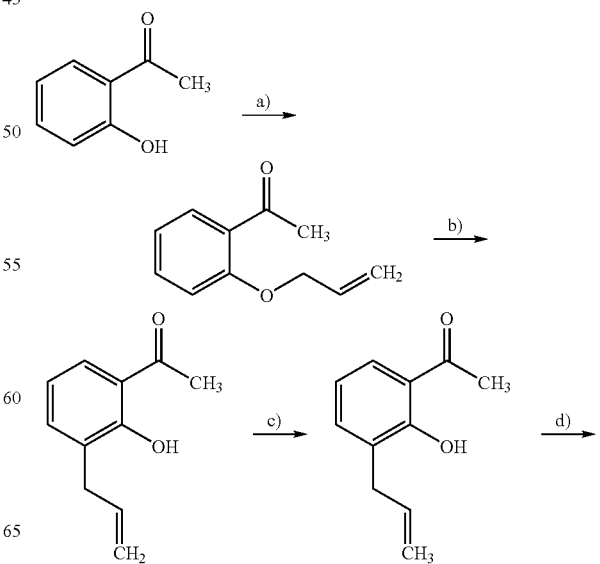

Scheme 1

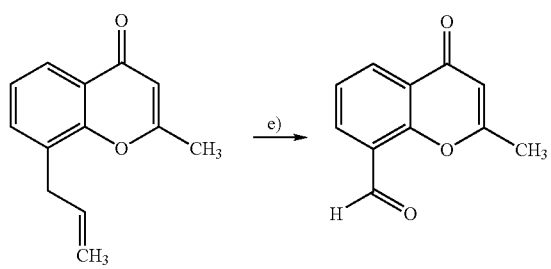

[a]: Allyl bromide, potassium carbonate, cat. potassium iodide, acetone, reflux; b): 230° C., 4 h; c): bis(benzonitrile)dichloropalladium (II), toluene, 120° C., 16 h; d): acetyle chloride, sodium hydride, THF, 10-25° C., 16 h; e): 1. ozone, dichloromethane, -60° C., 30 min; 2. dimethyl sulfide].

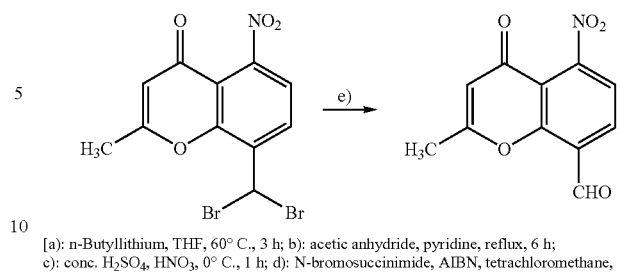

[a): n-Butyllithium, THF, 60° C., 3 h; b): acetic anhydride, pyridine, reflux, 6 h; c): conc. $H_2SO_4$, $HNO_3$, 0° C., 1 h; d): N-bromosuccinimide, AIBN, tetrachloromethane, reflux; e): N-methylmorpholine N-oxide, acetonitrile, reflux].

Scheme 2

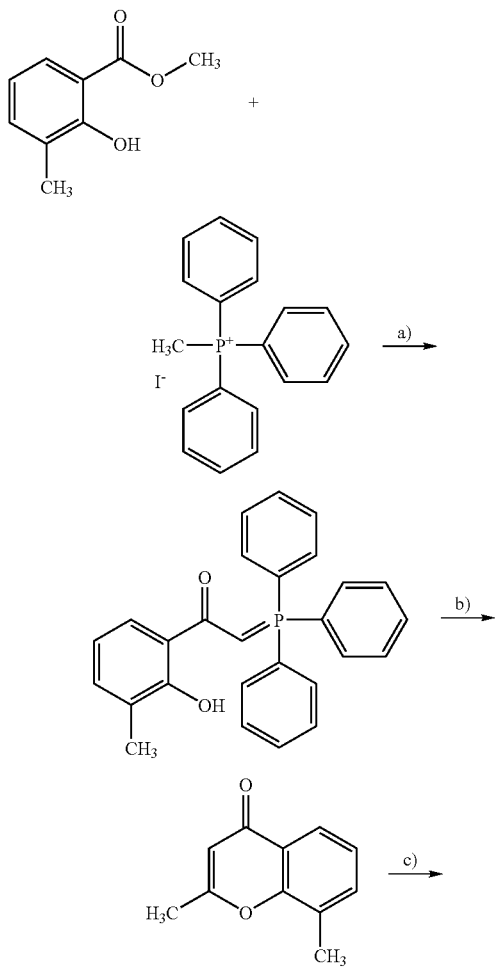

Scheme 3

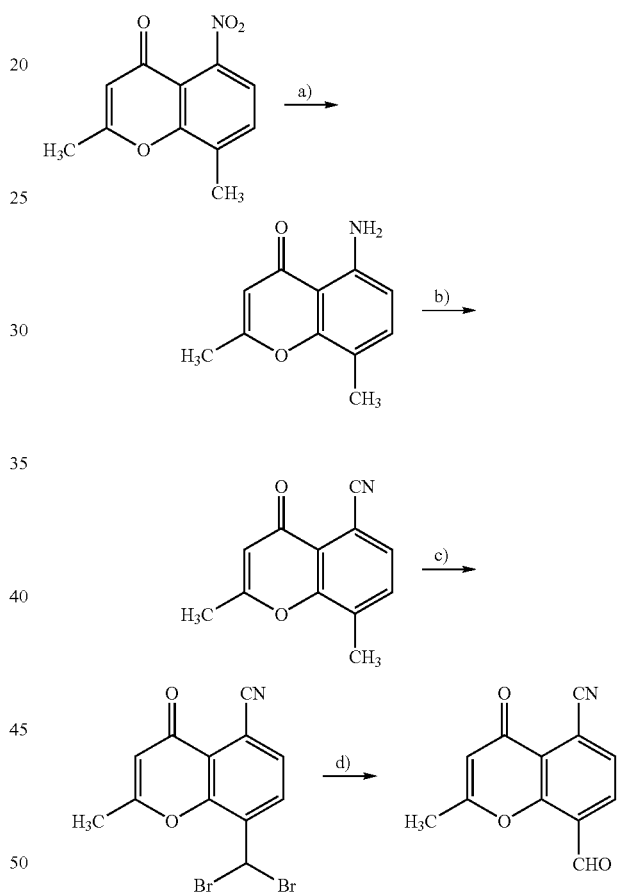

[a): Tin(II) chloride dihydrate, ethyl acetate, 70° C.; b): 1. sodium nitrite, sulfuric acid, 0° C., 1.5 h; 2. copper(I) cyanide, sodium cyanide, water/ethyl acetate, 0° C., 45 min; c): N-bromosuccinimide, AIBN, tetrachloromethane, reflux; d): N-methylmorpholine N-oxide, acetonitrile, reflux].

Scheme 4

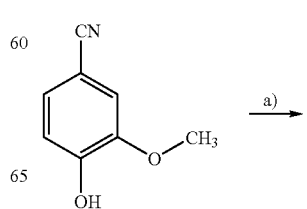

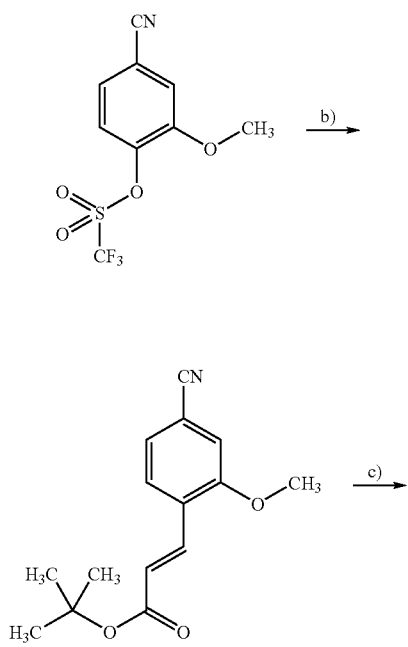

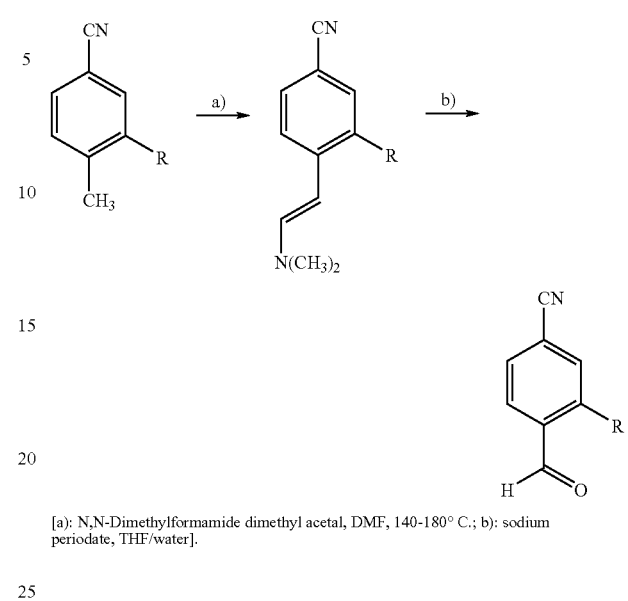

[a]: N,N-Dimethylformamide dimethyl acetal, DMF, 140-180° C.; b): sodium periodate, THF/water].

[a]: Trifluoromethanesulfonic anhydride, pyridine, 0° C. → RT, 30 min; b): tert-butyl acrylate, bis(triphenylphosphine)dichloropalladium (II), DMF, 120° C., 24 h; c): cat. osmium tetroxide, cat. benzyltriethylammonium chloride, sodium periodate, THF/water, 20-25° C., 2 h].

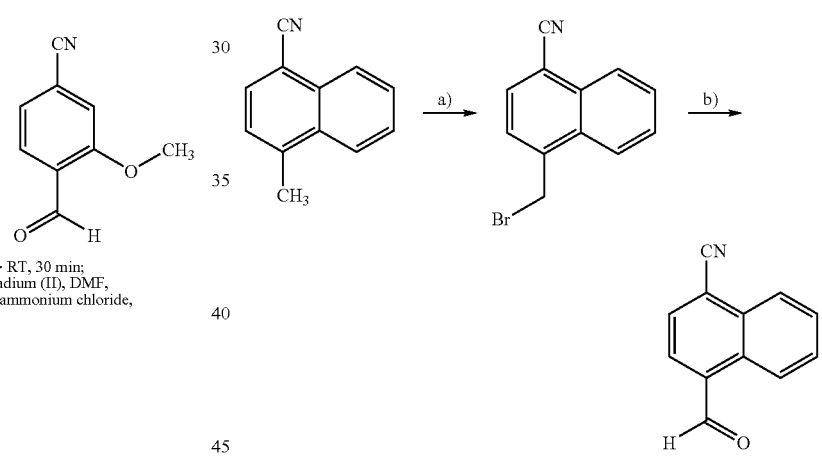

[a]: N-Bromosuccinimide, AIBN, tetrachloromethane, reflux; b): N-methylmorpholine N-oxide, acetonitrile, 3 Å molecular sieves].

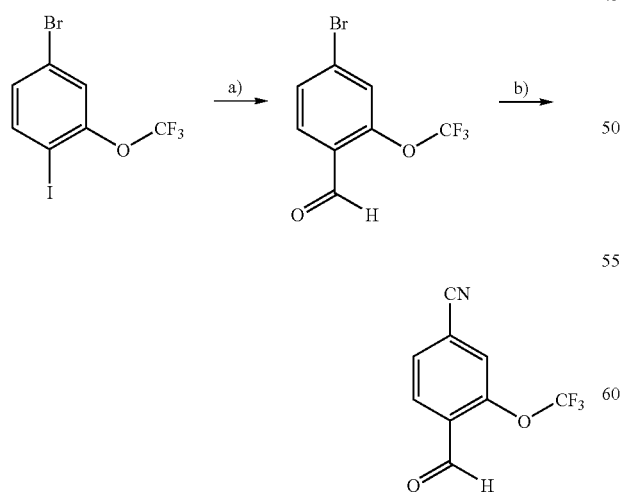

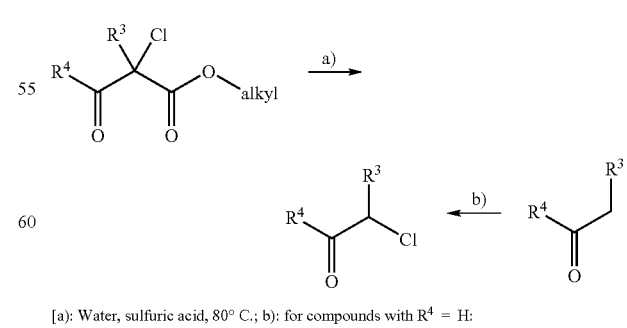

[a]: n-Butyllithium, THF, -78° C., then N-formylmorpholine; b): zinc cyanide, tetrakis(triphenylphosphine) palladium (0), DMF, microwave 250° C./5min].

[a]: Water, sulfuric acid, 80° C.; b): for compounds with $R^4$ = H: prolinamide, N-chlorosuccinimide, dichloromethane, RT; cf. N. Halland et al., *J. Am. Chem. Soc.* 126, 4790-4791 (2004)].

Scheme 9

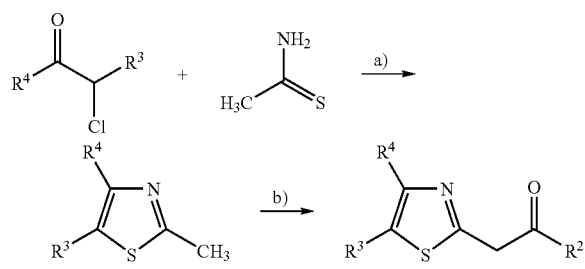

[a]: Benzene or ethanol, optionally triethylamine, reflux; b): 1. n-butyllithium, THF, -78° C.; 2. $R^2$—CO—Oalkyl, THF, -78° C.→RT].

Scheme 10

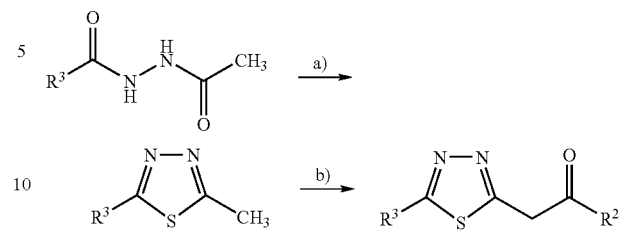

[a]: $P_2S_5$; cf. H. Lund, *Acta Chem. Scand.* 27, 391-395 (1973); b): 1. sodium hydride, toluene, 50° C.; $R^2$—CO—Oalkyl, THF, reflux].

Scheme 11

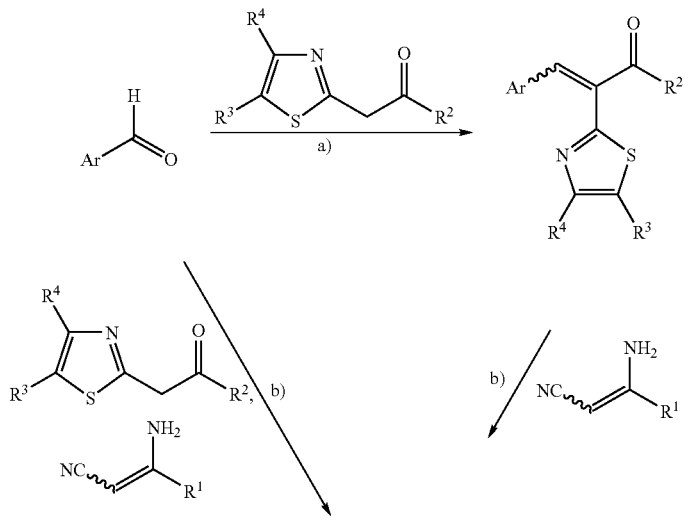

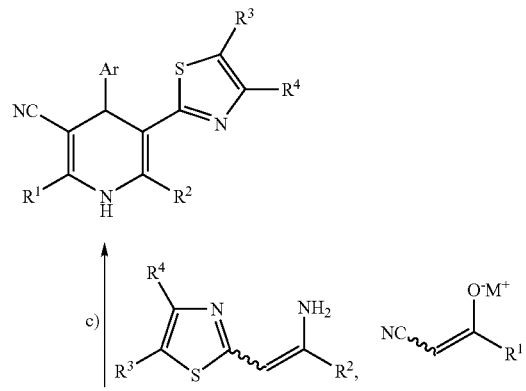

[a): Cat. piperidine/acetic acid, dichlormethane, reflux, 24 h; b): isopropanol, optionally potassium tert-butoxide, reflux, 12 h; c): isopropanol, acetic acid, reflux, 12 h ($M^+$ = $Li^+$, $Na^+$ or $K^+$)].

The compounds of the invention act as antagonists of the mineralocorticoid receptor and show a valuable range of pharmacological effects which could not have been predicted. They are therefore suitable for use as medicaments for the treatment and/or prophylaxis of diseases in humans and animals.

The compounds of the invention are suitable for the prophylaxis and/or treatment of various disorders and disease-related conditions, especially of disorders which are characterized either by an elevation of the plasma aldosterone concentration or by a change in the plasma aldosterone concentration relative to the plasma renin concentration, or are associated with these changes. Examples which may be mentioned are: idiopathic primary hyperaldosteronism, hyperaldosteronism associated with adrenal hyperplasia, adrenal adenomas and/or adrenal carcinomas, hyperaldosteronism associated with cirrhosis of the liver, hyperaldosteronism associated with heart failure, and (relative) hyperaldosteronism associated with essential hypertension.

The compounds of the invention are also suitable, because of their mechanism of action, for the prophylaxis of sudden cardiac death in patients at increased risk of dying of sudden cardiac death. These are in particular patients suffering for example from one of the following disorders: hypertension, heart failure, coronary heart disease, stable and unstable angina pectoris, myocardial ischemia, myocardial infarction, dilated cardiomyopathies, shock, arteriosclerosis, atrial and ventricular arrhythmia, transient and ischemic attacks, stroke, inflammatory cardiovascular disorders, peripheral and cardiac vascular disorders, peripheral blood flow disturbances, pulmonary hypertension, spasms of the coronary arteries and peripheral arteries, thromboses, thromboembolic disorders, and vasculitis.

The compounds of the invention can additionally be used for the prophylaxis and/or treatment of edema formation, such as, for example, pulmonary edema, renal edema or heart failure-related edema, and of restenoses such as following thrombolysis therapies, percutaneous transluminal angioplasties (PTA) and transluminal coronary angioplasties (PTCA), heart transplants and bypass operations.

The compounds of the invention are further suitable for use as diuretic and for electrolyte disturbances such as, for example, hypercalcemia.

The compounds of the invention can additionally be employed for the prophylaxis and/or treatment of diabetes mellitus and diabetic sequelae such as, for example, neuropathy and nephropathy, of acute and chronic renal failure and chronic renal insufficiency.

The present invention further relates to the use of the compounds of the invention for the treatment and/or prevention of disorders, especially of the aforementioned disorders.

The present invention further relates to the use of the compounds of the invention for the manufacture of a medicament for the treatment and/or prevention of disorders, especially of the aforementioned disorders.

The present invention further relates to a method for the treatment and/or prevention of disorders, especially of the aforementioned disorders, by using an effective amount of at least one of the compounds of the invention.

The compounds of the invention can be employed alone or, if required, in combination with other active ingredients. The present invention further relates to medicaments comprising at least one of the compounds of the invention and one or more further active ingredients, especially for the treatment and/or prevention of the aforementioned disorders. Suitable active ingredients which may be mentioned for combinations are by way of example and preferably:

active ingredients which lower blood pressure, for example and preferably from the group of calcium antagonists, angiotensin AII antagonists, ACE inhibitors, endothelin antagonists, renin inhibitors, alpha-receptor blockers, beta-receptor blockers and Rho kinase inhibitors;

diuretics, especially loop diuretics, and thiazides and thiazide-like diuretics;

agents having an antithrombotic effect, for example and preferably from the group of platelet aggregation inhibitors, of anticoagulants or of profibrinolytic substances;

active ingredients which alter lipid metabolism, for example and preferably from the group of thyroid receptor agonists, cholesterol synthesis inhibitors such as by way of example and preferably HMG-CoA reductase inhibitors or squalene synthesis inhibitors, of ACAT inhibitors, CETP inhibitors, MTP inhibitors, PPAR-alpha, PPAR-gamma and/or PPAR-delta agonists, cholesterol absorption inhibitors, lipase inhibitors, polymeric bile adsorbents, bile acid reabsorption inhibitors and lipoprotein(a) antagonists;

organic nitrates and NO donors such as, for example, sodium nitroprusside, nitroglycerin, isosorbide mononitrate, isosorbide dinitrate, molsidomine or SIN-1, and inhaled NO;

compounds having a positive inotropic effect, such as, for example, cardiac glycosides (digoxin), beta-adrenergic and dopaminergic agonists such as isoproterenol, adrenaline, noradrenaline, dopamine and dobutamine;

compounds which inhibit the degradation of cyclic guanosine monophosphate (cGMP) and/or cyclic adenosine monophosphate (cAMP), such as, for example, inhibitors of phosphodiesterases (PDE) 1, 2, 3, 4 and/or 5, especially PDE 5 inhibitors such as sildenafil, vardenafil and tadalafil, and PDE 3 inhibitors such as amrinone and milrinone;

natriuretic peptides such as, for example, atrial natriuretic peptide (ANP, anaritide), B-type natriuretic peptide or brain natriuretic peptide (BNP, nesiritide), C-type natriuretic peptide (CNP) and urodilatin;

calcium sensitizers such as by way of example and preferably levosimendan;

potassium supplements;

NO-independent but heme-dependent stimulators of guanylate cyclase such as in particular the compounds described in WO 00/06568, WO 00/06569, WO 02/42301 and WO 03/095451;

NO- and heme-independent activators of guanylate cyclase, such as in particular the compounds described in WO 01/19355, WO 01/19776, WO 01/19778, WO 01/19780, WO 02/070462 and WO 02/070510;

inhibitors of human neutrophil elastase (HNE), such as, for example, sivelestat or DX-890 (reltran);

compounds which inhibit the signal transduction cascade, such as, for example, tyrosine kinase inhibitors, in particular sorafenib, imatinib, gefitinib and erlotinib; and/or compounds which influence the energy metabolism of the heart, such as by way of example and preferably etomoxir, dichloroacetate, ranolazine or trimetazidine.

In a preferred embodiment of the invention, the compounds of the invention are administered in combination with a diuretic such as by way of example and preferably furosemide, bumetanide, torsemide, bendroflumethiazide, chlorthiazide, hydrochlorthiazide, hydroflumethiazide, methyclothiazide, polythiazide, trichlormethiazide, chlorthalidone, indapamide, metolazone, quinethazone, acetazolamide, dichlorophenamide, methazolamide, glycerol, isosorbide, mannitol, amiloride or triamterene.

Agents which lower blood pressure preferably mean compounds from the group of calcium antagonists, angiotensin AII antagonists, ACE inhibitors, endothelin antagonists, renin inhibitors, alpha-receptor blockers, beta-receptor blockers, Rho kinase inhibitors, and diuretics.

In a preferred embodiment of the invention, the compounds of the invention are administered in combination with a calcium antagonist such as by way of example and preferably nifedipine, amlodipine, verapamil or diltiazem.

In a preferred embodiment of the invention, the compounds of the invention are administered in combination with an angiotensin AII antagonist such as by way of example and preferably losartan, candesartan, valsartan, telmisartan or embusartan.

In a preferred embodiment of the invention, the compounds of the invention are administered in combination with an ACE inhibitor such as by way of example and preferably enalapril, captopril, lisinopril, ramipril, delapril, fosinopril, quinopril, perindopril or trandopril.

In a preferred embodiment of the invention, the compounds of the invention are administered in combination with an endothelin antagonist such as by way of example and preferably bosentan, darusentan, ambrisentan or sitaxsentan.

In a preferred embodiment of the invention, the compounds of the invention are administered in combination with a renin inhibitor such as by way of example and preferably aliskiren, SPP-600 or SPP-800.

In a preferred embodiment of the invention, the compounds of the invention are administered in combination with an alpha-1 receptor blocker such as by way of example and preferably prazosin.

In a preferred embodiment of the invention, the compounds of the invention are administered in combination with a beta-receptor blocker such as by way of example and preferably propranolol, atenolol, timolol, pindolol, alprenolol, oxprenolol, penbutolol, bupranolol, metipranolol, nadolol, mepindolol, carazalol, sotalol, metoprolol, betaxolol, celiprolol, bisoprolol, carteolol, esmolol, labetalol, carvedilol, adaprolol, landiolol, nebivolol, epanolol or bucindolol.

In a preferred embodiment of the invention, the compounds of the invention are administered in combination with a Rho kinase inhibitor such as by way of example and preferably fasudil, Y-27632, SLx-2119, BF-66851, BF-66852, BF-66853, KI-23095 or BA-1049.

Agents having an antithrombotic effect (antithrombotics) preferably mean compounds from the group of platelet aggregation inhibitors, of anticoagulants or of profibrinolytic substances.

In a preferred embodiment of the invention, the compounds of the invention are administered in combination with a platelet aggregation inhibitor such as by way of example and preferably aspirin, clopidogrel, ticlopidine or dipyridamole.

In a preferred embodiment of the invention, the compounds of the invention are administered in combination with a thrombin inhibitor such as by way of example and preferably ximelagatran, melagatran, bivalirudin or clexane.

In a preferred embodiment of the invention, the compounds of the invention are administered in combination with a GPIIb/IIIa antagonist such as by way of example and preferably tirofiban or abciximab.

In a preferred embodiment of the invention, the compounds of the invention are administered in combination with a factor Xa inhibitor such as by way of example and preferably rivaroxaban (BAY 59-7939), DU-176b, apixaban, otamixaban, fidexaban, razaxaban, fondaparinux, idraparinux, PMD-3112, YM-150, KFA-1982, EMD-503982, MCM-17, MLN-1021, DX 9065a, DPC 906, JTV 803, SSR-126512 or SSR-128428.

In a preferred embodiment of the invention, the compounds of the invention are administered in combination with heparin or a low molecular weight (LMW) heparin derivative.

In a preferred embodiment of the invention, the compounds of the invention are administered in combination with a vitamin K antagonist such as by way of example and preferably coumarin.

Agents which alter lipid metabolism preferably mean compounds from the group of CETP inhibitors, thyroid receptor agonists, cholesterol synthesis inhibitors such as HMG-CoA reductase inhibitors or squalene synthesis inhibitors, of ACAT inhibitors, MTP inhibitors, PPAR-alpha, PPAR-gamma and/or PPAR-delta agonists, cholesterol absorption inhibitors, polymeric bile acid adsorbents, bile acid reabsorption inhibitors, lipase inhibitors and lipoprotein(a) antagonists.

In a preferred embodiment of the invention, the compounds of the invention are administered in combination with a CETP inhibitor such as by way of example and preferably torcetrapib (CP-529 414), JJT-705, BAY 60-5521, BAY 78-7499 or CETP vaccine (Avant).

In a preferred embodiment of the invention, the compounds of the invention are administered in combination with a thyroid receptor agonist such as by way of example and preferably D-thyroxine, 3,5,3'-triiodothyronine (T3), CGS 23425 or axitirome (CGS 26214).

In a preferred embodiment of the invention, the compounds of the invention are administered in combination with an HMG-CoA reductase inhibitor from the class of statins such as by way of example and preferably lovastatin, simvastatin, pravastatin, fluvastatin, atorvastatin, rosuvastatin, cerivastatin or pitavastatin.

In a preferred embodiment of the invention, the compounds of the invention are administered in combination with a squalene synthesis inhibitor such as by way of example and preferably BMS-188494 or TAK-475.

In a preferred embodiment of the invention, the compounds of the invention are administered in combination with an ACAT inhibitor such as by way of example and preferably avasimibe, melinamide, pactimibe, eflucimibe or SMP-797.

In a preferred embodiment of the invention, the compounds of the invention are administered in combination with an MTP inhibitor such as by way of example and preferably implitapide, BMS-201038, R-103757 or JTT-130.

In a preferred embodiment of the invention, the compounds of the invention are administered in combination with a PPAR-gamma agonist such as by way of example and preferably pioglitazone or rosiglitazone.

In a preferred embodiment of the invention, the compounds of the invention are administered in combination with a PPAR-delta agonist such as by way of example and preferably GW-501516 or BAY 68-5042.

In a preferred embodiment of the invention, the compounds of the invention are administered in combination with a cholesterol absorption inhibitor such as by way of example and preferably ezetimibe, tiqueside or pamaqueside.

In a preferred embodiment of the invention, the compounds of the invention are administered in combination with a lipase inhibitor such as by way of example and preferably orlistat.

In a preferred embodiment of the invention, the compounds of the invention are administered in combination with a polymeric bile acid adsorbent such as by way of example and preferably cholestyramine, colestipol, colesolvam, Cholesta-Gel or colestimide.

In a preferred embodiment of the invention, the compounds of the invention are administered in combination with a bile acid reabsorption inhibitor such as by way of example and preferably ASBT (=IBAT) inhibitors such as, for example, AZD-7806, S-8921, AK-105, BARI-1741, SC-435 or SC-635.

In a preferred embodiment of the invention, the compounds of the invention are administered in combination with a lipoprotein(a) antagonist such as by way of example and preferably gemcabene calcium (CI-1027) or nicotinic acid.

The present invention further relates to medicaments which comprise at least one compound of the invention, normally together with one or more inert, non-toxic, pharmaceutically suitable excipients, and to the use thereof for the aforementioned purposes.

The compounds of the invention may have systemic and/or local effects. For this purpose, they can be administered in a suitable way such as, for example, by the oral, parenteral, pulmonary, nasal, sublingual, lingual, buccal, rectal, dermal, transdermal, conjunctival or otic route or as implant or stent.

The compounds of the invention can be administered in administration forms suitable for these administration routes.

Suitable for oral administration are administration forms which function according to the prior art and deliver the compounds of the invention rapidly and/or in a modified manner, and which contain the compounds of the invention in crystalline and/or amorphized and/or dissolved form, such as, for example, tablets (uncoated and coated tablets, for example having coatings which are resistant to gastric juice or are insoluble or dissolve with a delay and control the release of the compound of the invention), tablets which disintegrate rapidly in the mouth, or films/wafers, films/lyophilizates, capsules (for example hard or soft gelatin capsules), sugar-coated tablets, granules, pellets, powders, emulsions, suspensions, aerosols or solutions.

Parenteral administration can take place with avoidance of an absorption step (e.g. intravenous, intraarterial, intracardiac, intraspinal or intralumbar) or with inclusion of an absorption (e.g intramuscular, subcutaneous, intracutaneous, percutaneous, or intraperitoneal). Administration forms suitable for parenteral administration are, inter alia, preparations for injection and infusion in the form of solutions, suspensions, emulsions, lyophilizates or sterile powders.

Suitable for the other routes of administration are, for example, pharmaceutical forms for inhalation (inter alia powder inhalers, nebulizers), nasal drops, solutions, sprays; tablets for lingual, sublingual or buccal administration, films/wafers or capsules, suppositories, preparations for the ears and eyes, vaginal capsules, aqueous suspensions (lotions, shaking mixtures), lipophilic suspensions, ointments, creams, transdermal therapeutic systems (for example patches), milk, pastes, foams, dusting powders, implants or stents.

Oral or parenteral administration are preferred, especially oral and intravenous administration.

The compounds of the invention can be converted into the stated administration forms. This can take place in a manner known per se by mixing with inert, non-toxic, pharmaceutically suitable excipients. These excipients include inter alia carriers (for example microcrystalline cellulose, lactose, mannitol), solvents (e.g. liquid polyethylene glycols), emulsifiers and dispersants or wetting agents (for example sodium dodecyl sulfate, polyoxysorbitan oleate), binders (for example polyvinylpyrrolidone), synthetic and natural polymers (for example albumin), stabilizers (e.g. antioxidants such as, for example, ascorbic acid), colorings (e.g. inorganic pigments such as, for example, iron oxides) and masking flavors and/or odors.

It has generally proved to be advantageous on parenteral administration to administer amounts of about 0.001 to 1 mg/kg, preferably about 0.01 to 0.5 mg/kg of body weight per day to achieve effective results. On oral administration, the dosage is about 0.01 to 100 mg/kg, preferably about 0.01 to 20 mg/kg, and very particularly preferably about 0.1 to 10 mg/kg of body weight.

It may nevertheless be necessary where appropriate to deviate from the stated amounts, in particular as a function of body weight, administration route, individual response to the active ingredient, type of preparation and time or interval over which administration takes place. Thus, in some cases it may be sufficient to make do with less than the aforementioned minimum amount, whereas in other cases the upper limit mentioned must be exceeded. Where relatively large amounts are administered, it may be advisable to distribute these in a plurality of single doses over the day.

The following exemplary embodiments illustrate the invention. The invention is not restricted to the examples.

The percentage data in the following tests and examples are, unless indicated otherwise, percentages by weight; parts are parts by weight. Solvent ratios, dilution ratios and concentration data of liquid/liquid solutions are based in each case on the volume.

A. EXAMPLES

Abbreviations and Acronyms

| | |
|---|---|
| abs. | absolute |
| AIBN | 2,2'-azobis-2-methylpropanenitrile |
| cat. | catalytic |
| CI | chemical ionization (in MS) |
| conc. | concentrated |
| d | day(s) |
| DMF | dimethylformamide |
| DMSO | dimethyl sulfoxide |
| ee | enantiomeric excess |
| EI | electron impact ionization (in MS) |
| ent | enantiomer/enantiopure |
| eq | equivalent(s) |
| ESI | electrospray ionization (in MS) |
| GC-MS | coupled gas chromatography-mass spectrometry |
| h | hour(s) |
| HPLC | high pressure, high performance liquid chromatography |
| LC-MS | coupled liquid chromatography-mass spectrometry |
| min | minute(s) |
| MPLC | medium pressure liquid chromatography |
| MS | mass spectrometry |
| NMR | nuclear magnetic resonance spectrometry |
| $R_f$ | retention index (in TLC) |
| $R_t$ | retention time (in HPLC) |
| RT | room temperature |
| THF | tetrahydrofuran |
| TLC | thin-layer chromatography |
| v/v | volume-to-volume ratio (of a solution) |

LC-MS, GC-MS and HPLC Methods:

Method 1 (LC-MS):

MS instrument type: Micromass ZQ; HPLC instrument type: HP 1100 Series; UV DAD; column: Phenomenex Gemini 3μ 30 mm×3.00 mm; eluent A: 1 l of water+0.5 ml of 50% formic acid, eluent B: 1 l of acetonitrile+0.5 ml of 50% formic acid; gradient: 0.0 min 90% A→2.5 min 30% A→3.0 min 5% A→4.5 min 5% A; flow rate: 0.0 min 1 ml/min→2.5 min/3.0 min/4.5 min 2 ml/min; oven: 50° C.; UV detection: 210 nm Method 2 (GC-MS):

Instrument: Micromass GCT, GC 6890; column: Restek RTX-35, 15 m×200 μm×0.33 μm; constant flow with helium: 0.88 ml/min; oven: 70° C.; inlet: 250° C.; gradient: 70° C., 30° C./min→310° C. (hold for 3 min)

Method 3 (LC-MS):

MS instrument type: Micromass ZQ; HPLC instrument type: Waters Alliance 2795; column: Phenomenex Synergi 2μ Hydro-RP Mercury 20 mm×4 mm; eluent A: 1 l of water+0.5 ml of 50% formic acid, eluent B: 1 l of acetonitrile+0.5 ml of 50% formic acid; gradient 0.0 min 90% A→2.5 min 30% A→3.0 min 5% A→4.5 min 5% A; flow rate: 0.0 min 1 ml/min→2.5 min/3.0 min/4.5 min 2 ml/min; oven: 50° C.; UV detection: 210 nm.

Method 4 (LC-MS):

Instrument: Micromass Quattro LCZ with HPLC Agilent Series 1100; column: Phenomenex Onyx Monolithic C18, 100 mm×3 mm; eluent A: 1 l of water+0.5 ml of 50% formic acid, eluent B: 1 l of acetonitrile+0.5 ml of 50% formic acid; gradient: 0.0 min 90% A→2 min 65% A→4.5 min 5% A→6 min 5% A; flow rate: 2 ml/min; oven: 40° C.; UV detection: 208-400 nm.

Method 5 (LC-MS):

Instrument: Micromass Quattro LCZ with HPLC Agilent Series 1100; column: Phenomenex Synergi 2μ Hydro-RP Mercury 20 mm×4 mm; eluent A: 1 l of water+0.5 ml of 50% formic acid, eluent B: 1 l of acetonitrile+0.5 ml of 50% formic acid; gradient: 0.0 min 90% A→2.5 min 30% A→3.0 min 5% A→4.5 min 5% A; flow rate: 0.0 min 1 ml/min→2.5 min/3.0 min/4.5 min 2 ml/min; oven: 50° C.; UV detection: 208-400 nm.

Method 6 (GC-MS):

Instrument: Micromass GCT, GC 6890; column: Restek RTX-35, 15 m×200 μm×0.33 μm; constant flow with helium: 0.88 ml/min; oven: 70° C.; inlet: 250° C.; gradient: 70° C., 30° C./min→310° C. (hold for 12 min)

Method 7 (LC-MS):

Instrument: Micromass Platform LCZ with HPLC Agilent Series 1100; column: Thermo Hypersil GOLD 3μ 20 mm×4 mm; eluent A: 1 l of water+0.5 ml of 50% formic acid, eluent B: 1 l of acetonitrile+0.5 ml of 50% formic acid; gradient: 0.0 min 100% A→0.2 min 100% A→2.9 min 30% A→3.1 min 10% A→5.5 min 10% A; oven: 50° C.; flow rate: 0.8 ml/min; UV detection: 210 nm.

Method 8 (LC-MS):

MS instrument type: Waters ZQ; HPLC instrument type: Waters Alliance 2795; column: Merck Chromolith RP18e, 100 mm×3 mm; eluent A: 1 l of water+0.5 ml of 50% formic acid, eluent B: 1 l of acetonitrile+0.5 ml of 50% formic acid; gradient: 0.0 min 90% A→2 min 65% A→4.5 min 5% A→6 min 5% A; flow rate: 2 ml/min; oven: 40° C.; UV detection: 210 nm.

Starting Compounds and Intermediates

Example 1A

4-Cyano-2-methoxyphenyl trifluoromethanesulfonate

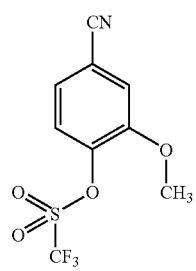 [SMILES: COc1cc(C#N)ccc1OS(=O)(=O)C(F)(F)F]

24 ml (141 mmol) of trifluoromethanesulfonic anhydride are slowly added dropwise to a solution of 20 g (134 mmol) of 4-hydroxy-3-methoxybenzonitrile in pyridine (80 ml), keeping the reaction temperature below 25° C. with the aid of an ice bath. The suspension is then stirred at RT for 1 h. Ice water (400 ml) is added, and the suspension is stirred further until room temperature is reached. It is then filtered, the solid is dissolved in ethyl acetate, and the solution is washed with saturated sodium chloride solution. The organic phase is dried over magnesium sulfate and concentrated. 37.13 g (92% of theory) of the title compound are obtained as a white solid.

LC-MS (Method 1): $R_t$=2.54 min; MS (EIpos): m/z=282 [M+H]$^+$ $^1$H-NMR (300 MHz, DMSO-d$_6$): δ=3.97 (s, 3H), 7.60 (dd, 1H), 7.71 (d, 1H), 7.92 (d, 1H).

Example 2A tert-Butyl (2E)-3-(4-cyano-2-methoxyphenyl)acrylate

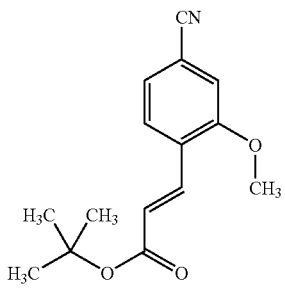 [SMILES: COc1cc(C#N)ccc1/C=C/C(=O)OC(C)(C)C]

4 g (5.7 mmol) of bis(triphenylphosphine)palladium(II) chloride are added to a degassed solution of 37.13 g (132 mmol) of 4-cyano-2-methoxyphenyl trifluoromethanesulfonate, 35 ml (245 mmol) of tert-butyl acrylate and 90 ml (645 mmol) of triethylamine in DMF (250 ml). The solution is stirred under a protective gas atmosphere at 100° C. for 24 h. Ice water (1000 ml) is then added, and the suspension is extracted with ethyl acetate ((3×100 ml). The organic phase is washed with saturated sodium chloride solution, dried over magnesium sulfate and concentrated. The residue is purified by column chromatography (silica gel, mobile phase: cyclohexane-ethyl acetate 10:1). 24.6 g (72% of theory) of the title compound are obtained as a white solid.

LC-MS (Method 3): $R_t$=2.59 min; MS (EIpos): m/z=260 [M+H]$^+$

¹H-NMR (300 MHz, DMSO-d₆): δ=1.48 (s, 9H), 3.93 (s, 3H), 6.65 (d, 1H), 7.42 (d, 1H), 7.58 (s, 1H), 7.74 (d, 1H), 7.89 (d, 1H).

Example 3A

4-Formyl-3-methoxybenzonitrile

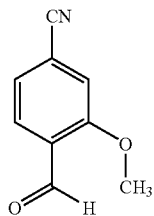

79 g (370 mmol) of sodium metaperiodate are added in portions to a vigorously stirred solution of 48 g (185 mmol) of tert-butyl (2E)-3-(4-cyano-2-methoxyphenyl)acrylate, 207 mg (0.81 mmol) of osmium tetroxide and 1.4 g (6.14 mmol) of benzyltriethylammonium chloride in 750 ml of water/THF (2:1), keeping the reaction temperature below 30° C. The solution is stirred further at RT for 1 h. Water (2000 ml) is added, and the mixture is then filtered. The remaining solid is dissolved in ethyl acetate, and the solution is washed with saturated sodium chloride solution. The organic phase is dried over magnesium sulfate and concentrated. The residue is stirred with petroleum ether. 21.18 g (71% of theory) of the title compound are obtained as a white solid.

LC-MS (Method 1): $R_t$=1.87 min; MS (Elpos): m/z=162 [M+H]⁺

¹H-NMR (300 MHz, DMSO-d₆): δ=3.98 (s, 3H), 7.53 (d, 1H), 7.80 (s, 1H), 7.81 (d, 1H), 10.37 (s, 1H).

Example 4A 1-(4-Methyl-1,3-thiazol-2-yl)acetone

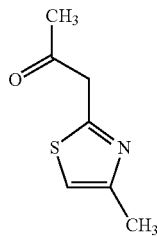

5.00 g (44.2 mmol) of 2,4-dimethylthiazole are dissolved in 50 ml of THF and, at −78° C., 19.4 ml (48.6 mmol) of n-butyllithium (2.5 M solution in hexane) are added dropwise. After stirring at −78° C. for 2 hours, 6.62 g (75.1 mmol) of ethyl acetate are added as solution in 25 ml of abs. THF. The mixture is stirred at −78° C. for 1 h and then warmed to room temperature. It is then hydrolyzed with sodium bicarbonate solution, and the mixture is extracted three times with diethyl ether. The combined organic phases are dried with magnesium sulfate, and the solvent is removed in a rotary evaporator. The crude product is purified by column chromatography (silica gel, mobile phase, cyclohexane/ethyl acetate 5:1). 3.2 g (47% of theory) of the title compound are obtained.

GC-MS (Method 2): $R_t$=3.87 min; MS (Elpos): m/z=155 [M]⁺

¹H-NMR (300 MHz, CDCl₃): δ [ppm]=2.27 (s, 3H), 2.44 (s, 3H), 4.10 (s, 2H), 6.84 (s, 1H).

Example 5A 1-(4-Methyl-1,3-thiazol-2-yl)butan-2-one

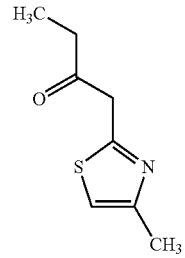

3.00 g (26.5 mmol) of 2,4-dimethylthiazole are dissolved in 30 ml of THF and, at −78° C., 11.6 ml (29.2 mmol) of n-butyllithium (2.5 M solution in hexane) are added dropwise. After stirring at −78° C. for 2 hours, 4.60 g (45.1 mmol) of ethyl propionate are added as solution in 15 ml of abs. THF. The mixture is stirred at −78° C. for 1 h and then warmed to room temperature. It is then hydrolyzed with sodium bicarbonate solution, and the mixture is extracted three times with diethyl ether. The combined organic phases are dried with magnesium sulfate, and the solvent is removed in a rotary evaporator. 3.5 g (39% of theory) of the title compound are obtained in 50% purity (GC-MS) and are employed without further purification.

GC-MS (Method 2): $R_t$=4.30 min; MS (Elpos): m/z=169 [M]⁺.

Example 6A

3-Methoxy-4-[2-(4-methyl-1,3-thiazol-2-yl)-3-oxobut-1-en-1-yl]benzonitrile

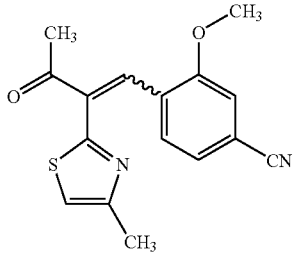 [SMILES: COc1cc(C#N)ccc1C=C(C(C)=O)c1nc(C)cs1]

400 mg (2.48 mmol) of the compound from example 3A and 424 mg (2.73 mmol) of the compound from example 4A are dissolved in 10 ml of dichloromethane, and 0.245 ml (2.48 mmol) of piperidine and 0.142 ml (2.48 mmol) of acetic acid are added. The reaction mixture is heated under reflux with an inverse water trap overnight. The volatile components are then removed in a rotary evaporator, and the crude product is purified by preparative HPLC (eluent: acetonitrile/water with 0.1% formic acid, gradient 20:80→95:5). 390 mg (53% of theory) of the title compound are obtained as a mixture of the E/Z isomers.

LC-MS (Method 4): $R_t$=3.13 min and 3.52 min; MS (El-pos): m/z each=299 [M+H]$^+$.

Example 7A

1-[2-(Allyloxy)phenyl]ethanone

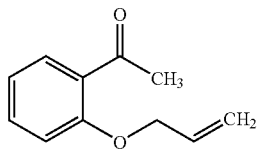

542 g (3.9 mol) of 2-hydroxyacetophenone are heated with 592 g (4.9 mol) of allyl bromide, 1000 g (7.2 mol) of potassium carbonate and 13.2 g (79 mmol) of potassium iodide in 2.4 liters of acetone under reflux for 24 h. Cooling to room temperature is followed by filtration, and the solvent is removed in vacuo. The residue is dissolved in toluene and washed with 10% strength sodium hydroxide solution and water. Concentration results in 689 g (98% of theory) of the title compound.

$^1$H-NMR (300 MHz, CDCl$_3$): δ=2.68 (s, 3H), 4.68 (dd, 2H), 5.89 (dd, 2H), 6.09 (m, 1H), 6.99 (dd, 2H), 7.44 (m, 1H), 7.71 (d, 1H).

Example 8A 1-(3-Allyl-2-hydroxyphenyl)ethanone

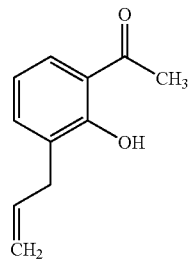

160 g (0.9 mol) of 1-[2-(allyloxy)phenyl]ethanone are stirred at 230-240° C. in a metal bath for 4 h. After cooling to room temperature, the product is distilled through a thin-film evaporator at 140° C. and 0.4 mbar. 155 g (97% of theory) of the title compound are obtained.

$^1$H-NMR (300 MHz, CDCl$_3$): δ=2.68 (s, 3H), 3.44 (d, 2H), 5.09 (m, 2H), 6.01 (m, 1H), 6.85 (t, 1H), 7.38 (dd, 1H), 7.62 (dd, 1H), 12.61 (s, 1H).

Example 9A

1-{2-Hydroxy-3-[(1E)-prop-1-en-1-yl]phenyl}ethanone

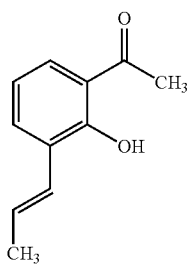

40 g (227 mmol) of 1-(3-allyl-2-hydroxyphenyl)ethanone are dissolved in 120 ml of toluene, and 2.17 g (5.6 mmol) of bis(benzonitrile)dichloropalladium(II) are added. The reaction mixture is heated at 120° C. overnight. Cooling to room temperature is followed by filtration through kieselguhr, and the solvent is removed in vacuo. 20.9 g (95% of theory) of the title compound are obtained and are reacted in the next stage without further purification.

LC-MS (Method 3): $R_t$=2.36 min; m/z=177 [M+H]$^+$ $^1$H-NMR (300 MHz, CDCl$_3$): δ=1.91 (dd, 3H), 2.63 (s, 3H), 6.32 (m, 1H), 6.73 (dd, 1H), 6.85 (t, 1H), 7.59 (m, 2H), 12.74 (s, 1H).

Example 10A

2-Methyl-8-[(1E)-prop-1-en-1-yl]-4H-chromen-4-one

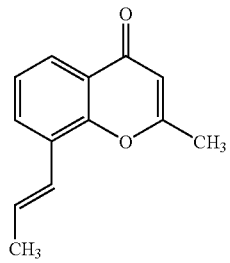

12.52 g (313.2 mmol) of 60% sodium hydride (suspension in mineral oil) are introduced under argon into 300 ml of absolute THF at 10° C. 18.4 g (104.4 mmol) of 1-{2-hydroxy-3-[(1E)-prop-1-en-1-yl]phenyl}ethanone are slowly added dropwise to the suspension. After 15 min, 9 g (114.9 mmol) of acetyl chloride are added. The reaction mixture is stirred at room temperature overnight. It is hydrolyzed with 300 ml of water and extracted several times with ethyl acetate. Washing of the organic phase with saturated sodium chloride solution is followed by drying over sodium sulfate. The solvent is then removed in vacuo. The residue is taken up in 200 ml of methanol and heated with 50 ml of 20% hydrochloric acid at 80° C. for 30 min The solvent is then removed in vacuo, and the residue is mixed with 400 ml of water. It is extracted several times with dichloromethane. After the organic phase has been dried over magnesium sulfate, the solvent is removed in vacuo, and the residue is purified by column chromatography (mobile phase: dichloromethane/methanol 98:2). 10.5 g (50.2% of theory) of the title compound are obtained as a yellow oil.

LC-MS (Method 5): $R_t$=2.07 min; m/z=201 [M+H]$^+$ $^1$H-NMR (300 MHz, CDCl$_3$): δ=1.98 (dd, 3H), 2.43 (s, 3H), 6.18 (s, 1H), 6.40 (m, 1H), 6.85 (dd, 1H), 7.31 (t, 1H), 7.72 (dd, 1H), 8.05 (dd, 1H).

Example 11A

2-Methyl-4-oxo-4H-chromene-8-carbaldehyde

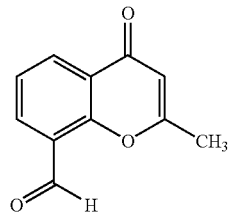

18.5 g (62.8 mmol) of 2-methyl-8-[(1E)-prop-1-en-1-yl]-4H-chromen-4-one are dissolved in 400 ml of dichloromethane and cooled to −60° C. Ozone is passed into the reaction solution for 30 min. Dimethyl sulfide is then added to the reaction mixture. After warming to room temperature, the solvent is removed in vacuo, and the residue is slurried in a little methanol. The solid remaining after filtration is recrystallized from diethyl ether. 9.1 g (77.4% of theory) of the title compound are obtained.

LC-MS (Method 5): $R_t$=1.47 min; MS (EIpos): m/z=189 [M+H]$^+$ $^1$H-NMR (300 MHz, CDCl$_3$): δ=2.48 (s, 3H), 6.27 (s, 1H), 7.51 (m, 1H), 8.21 (dd, 1H), 8.46 (dd, 1H), 10.67 (s, 1H).

Example 12A 1-(4-Methyl-1,3-thiazol-2-yl)pentan-2-one

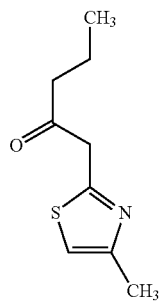

3.00 g (26.5 mmol) of 2,4-dimethylthiazole are dissolved in 30 ml of abs. THF and, at −78° C., 11.7 ml (29.2 mmol) of n-butyllithium (2.5 M solution in hexane) are added dropwise. After stirring at −78° C. for 2 hours, 5.23 g (45.1 mmol) of ethyl butyrate are added as solution in 15 ml of abs. THF. The mixture is stirred at −78° C. for 1 h and then warmed to room temperature. It is then hydrolyzed with sodium bicarbonate solution, and the mixture is extracted three times with diethyl ether. The combined organic phases are dried with magnesium sulfate, and the solvent is removed in a rotary evaporator. The crude product is purified by column chromatography (silica gel, mobile phase: cyclohexane/ethyl acetate 5:1). 3.0 g (62% of theory) of the title compound are obtained.

GC-MS (Method 6): $R_t$=4.63 min; MS (EIpos): m/z=183 [M]$^+$.

Example 13A

1-Methoxy-3-(4-methyl-1,3-thiazol-2-yl)acetone

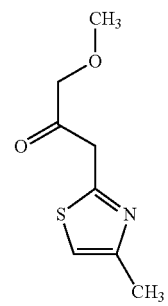

3.00 g (26.5 mmol) of 2,4-dimethylthiazole are dissolved in 30 ml of abs. THF and, at −78° C., 11.7 ml (29.2 mmol) of n-butyllithium (2.5 M solution in hexane) are added dropwise. After stirring at −78° C. for 2 hours, 5.32 g (45.1 mmol) of ethyl methoxyacetate are added as solution in 15 ml of abs. THF. The mixture is stirred at −78° C. for 1 h and then warmed to room temperature. It is then hydrolyzed with sodium bicarbonate solution, and the mixture is extracted three times with diethyl ether. The combined organic phases are dried with magnesium sulfate, and the solvent is removed in a rotary evaporator. 4.2 g (68% of theory) of the title compound are obtained in 80% purity (GC-MS) and are employed without further purification.

GC-MS (Method 6): $R_t$=4.86 min; MS (EIpos): m/z=185 [M]$^+$.

Example 14A

3-Methoxy-4-[4-methoxy-2-(4-methyl-1,3-thiazol-2-yl)-3-oxobut-1-en-1-yl]benzonitrile

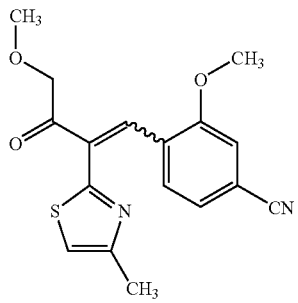 [SMILES: COCC(=O)C(=Cc1ccc(C#N)cc1OC)c1nc(C)cs1]

500 mg (3.10 mmol) of the compound from example 3A and 632 mg (3.41 mmol) of the compound from example 13A are dissolved in 15 ml of dichloromethane, and 0.307 ml (3.10 mmol) of piperidine and 0.178 ml (3.10 mmol) of acetic acid are added. The reaction mixture is heated under reflux with an inverse water trap overnight. The volatile components are removed in a rotary evaporator, and the crude product is purified by preparative HPLC (eluent: acetonitrile/water with 0.1% formic acid, gradient 20:80→95:5). 200 mg (20% of theory) of the title compound are obtained as a mixture of the E/Z isomers.

LC-MS (Method 1): $R_t$=2.31 and 2.39 min; MS (Elpos): m/z each=329 [M+H]$^+$.

Example 15A

1-Chlorobutan-2-one

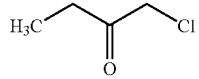

40.0 g (243 mmol) of methyl 2-chloro-3-oxopentanoate and 65 ml of conc. sulfuric acid are dissolved in 120 ml of water and heated at 80° C. overnight. After cooling, 300 ml of water are added, and the mixture is extracted three times with dichloromethane. The combined organic phases are dried over magnesium sulfate and concentrated in a rotary evaporator. The residue is then fractionally distilled under atmospheric pressure. The fraction boiling in the range of 138-140° C. affords 10.5 g (40% of theory) of the title compound.

GC-MS (Method 2): $R_t$=1.53 min; MS (Elpos): m/z=106 [M]$^+$ $^1$H-NMR (300 MHz, DMSO-d$_6$): δ=0.96 (t, 3H), 2.48-2.55 (q, 2H), 4.49 (s, 2H).

Example 16A

4-Ethyl-2-methyl-1,3-thiazole

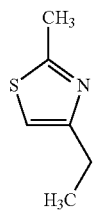

3.00 g (28.2 mmol) of the compound from example 15A and 2.12 g (28.2 mmol) of thioacetamide are heated in 25 ml of benzene under reflux with a water trap overnight. After cooling, 4.32 ml (30.97 mmol) of triethylamine are added. The mixture is stirred for 20 min, and the precipitated salt is removed by filtration. The solvent is then removed in a rotary evaporator. 1.73 g (48% of theory) of the title compound are obtained.

GC-MS (Method 2): $R_t$=2.34 min; MS (Elpos): m/z=127 [M]$^+$ $^1$H-NMR (300 MHz, CDCl$_3$): δ=1.28 (t, 3H), 2.68 (s, 3H), 2.77 (q, 2H), 6.69 (s, 1H).

Example 17A 1-(4-Ethyl-1,3-thiazol-2-yl)acetone

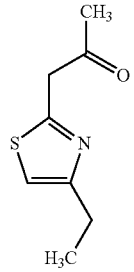

1.70 g (13.4 mmol) of the compound from example 16A are dissolved in 15 ml of abs. THF and, at −78° C., 5.88 ml (14.7 mmol) of n-butyllithium (2.5 M solution in hexane) are added dropwise. After stirring at −78° C. for 2 hours, 2.00 g (22.7 mmol) of ethyl acetate are added as a solution in 10 ml of abs. THF. The mixture is stirred at −78° C. for 1 h and then warmed to room temperature. It is then hydrolyzed with sodium bicarbonate solution, and the mixture is extracted three times with diethyl ether. The combined organic phases are dried with magnesium sulfate, and the solvent is removed in a rotary evaporator. 1.89 g (84% of theory) of the title compound are obtained. GC-MS (Method 2): $R_t$=4.20 min; MS (Elpos): m/z=169 [M]$^+$.

Example 18A

2-Methyl-4,5,6,7-tetrahydro-1,3-benzothiazole

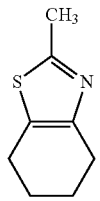

5.00 g (37.7 mmol) of 2-chlorocyclohexanone and 2.83 g (37.7 mmol) of thioacetamide are heated in 25 ml of ethanol at the reflux temperature overnight. After cooling, the volatile components are removed in a rotary evaporator, and the remaining residue is taken up in 2 N sodium carbonate solution. It is extracted three times with dichloromethane, and the combined organic phases are dried with magnesium sulfate. The solvent is removed in a rotary evaporator, and the residue is then purified by column chromatography (silica gel, mobile phase: cyclohexane/ethyl acetate 7:3). 3.35 g (58% of theory) of the title compound are obtained.

LC-MS (Method 7): $R_t$=2.49 min; MS (Elpos): m/z=154 [M+H]$^+$
$^1$H-NMR (300 MHz, CDCl$_3$): δ=1.84 (m, 4H), 2.63 (s, 3H), 2.67-2.77 (4H).

Example 19A 1-(4,5,6,7-Tetrahydro-1,3-benzothiazol-2-yl)acetone

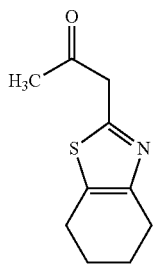

1.50 g (9.78 mmol) of the compound from example 18A are dissolved in 10 ml of abs. THF and, at −78° C., 4.31 ml (10.77 mmol) of n-butyllithium (2.5 M solution in hexane) are added dropwise. After stirring at −78° C. for 2 hours, 1.46 g (16.6 mmol) of ethyl acetate are added as solution in 5 ml of abs. THF. The mixture is stirred at −78° C. for 1 h and then warmed to room temperature. It is then hydrolyzed with sodium bicarbonate solution, and the mixture is extracted three times with diethyl ether. The combined organic phases are dried over magnesium sulfate, and the solvent is removed in a rotary evaporator. 1.60 g (67% of theory) of the title compound are obtained in 80% purity (LC-MS) and are employed without further purification.

LC-MS (Method 1): $R_t$=1.73 min; MS (Elpos): m/z=196 [M+H]$^+$.

Example 20A

3-Methoxy-4-[2-(4-methyl-1,3-thiazol-2-yl)-3-oxo-pent-1-en-1-yl]benzonitrile

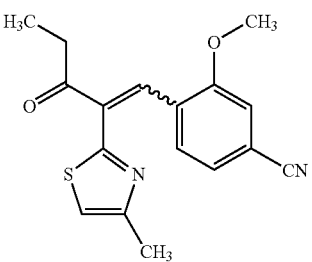 [SMILES: CCC(=O)C(=Cc1ccc(C#N)cc1OC)c1nc(C)cs1]

400 mg (2.48 mmol) of the compound from example 3A and 924 mg (2.73 mmol, 50% purity) of the compound from example 5A are dissolved in 10 ml of dichloromethane, and 0.245 ml (2.48 mmol) of piperidine and 0.142 ml (2.48 mmol) of acetic acid are added. The reaction mixture is heated under reflux with an inverse water trap overnight. The volatile components are removed in a rotary evaporator, and the crude product is purified by preparative HPLC (eluent: acetonitrile/water with 0.1% formic acid, gradient 20:80→95:5). 657 mg (83% of theory) of the title compound are obtained as a mixture of the E/Z isomers.

LC-MS (Method 1): $R_t$=2.36 and 2.56 min; MS (Elpos): m/z each=313 [M+H]$^+$.

Example 21A

3-Methylquinoline-5-carboxylic acid

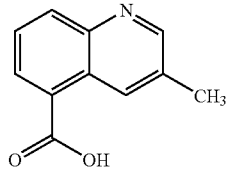

100.0 g (512 mmol) of 3-hydroxy-4-nitro-2-benzofuran-1 (3H)-one [cf. Watanabe et al., Chem. Pharm. Bull. 20, 2123-2126 (1972)] are dissolved in 410 ml of ethanol and hydrogenated in a Parr apparatus with 10.3 g of palladium on carbon (5%) under a hydrogen pressure of 3 bar. With this very exothermic reaction, the internal temperature is controlled via the supply of hydrogen; thus, when an internal temperature of 75° C. is reached, the hydrogen supply is stopped. After the reaction has subsided and the internal temperature has fallen to about 40° C., 3 bar of hydrogen are again imposed. The procedure is repeated until no further consumption of hydrogen is detectable. The total duration of the reaction is about three hours. The catalyst is then filtered off through kieselguhr. The solution obtained in this way of the corresponding amine[4-amino-3-hydroxy-2-benzofuran-1(3H)-one] is mixed with 29.7 g (512 mmol) of propionaldehyde and stirred at the reflux temperature for 3 days. After cooling, the precipitated solid is filtered off with suction and washed with ethanol. Drying overnight results in 22.5 g (23% of theory) of the title compound.

MS (Elpos): m/z=188 [M+H]$^+$.
$^1$H-NMR (300 MHz, DMSO-d$_6$): δ=2.53 (s, 3H), 7.76 (dd, 1H), 8.18-8.26 (m, 2H), 8.84 (d, 1H), 9.05 (br. t, 1H), 13.27 (br. s, 1H).

Example 22A (3-Methylquinolin-5-yl)methanol

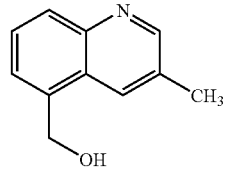

35.0 g (187 mmol) of the compound from example 21A are introduced into 440 ml of 1,2-dimethoxyethane, 32.3 ml (233 mmol) of triethylamine are added, and the mixture is stirred at room temperature for 30 min Then 22.3 ml (233 mmol) of ethyl chloroformate are added dropwise at 15° C., and the mixture is stirred at room temperature for 15 min. The precipitated solid is filtered off and washed with 1,2-dimethoxyethane. The filtrate is then concentrated, and the residue is taken up in 440 ml of ethanol. 13.1 g (345 mmol) of sodium borohydride are added dropwise as a solution in 210 ml of water to the solution obtained in this way. After a reaction time of 16 h at room temperature, the precipitated solid is filtered off with suction and washed with ethanol, and the filtrate is concentrated in a rotary evaporator. The resulting residue is taken up in 800 ml of water and 600 ml of dichloromethane/methanol (8:2). The aqueous phase is again extracted with 600 ml of dichloromethane/methanol (8:2), and the combined organic phases are washed with saturated sodium chloride solution. Concentration and drying result in 23.0 g (71% of theory) of the title compound.

$^1$H-NMR (300 MHz, DMSO-$d_6$): δ=2.48 (s, 3H), 4.99 (s, 2H), 5.41 (br. s, 1H), 7.56-7.69 (m, 2H), 7.92 (dd, 1H), 8.29 (m, 1H), 8.77 (d, 1H).

Example 23A

3-Methylquinoline-5-carbaldehyde

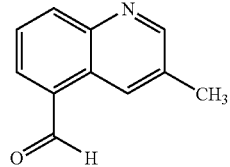

30.0 g (173 mmol) of the compound from example 22A are taken up in 850 ml of dichloromethane, and 240.0 g of manganese(IV) oxide are added. The mixture is stirred at room temperature for 16 h and then filtered through kieselguhr. The latter is washed with dichloromethane, and the filtrate is concentrated in a rotary evaporator. Drying the residue results in 23.0 g (75% of theory) of the title compound.

$^1$H-NMR (300 MHz, CDCl$_3$): δ=2.57 (s, 3H), 7.78 (dd, 1H), 8.00 (dd, 1H), 8.31 (d, 1H), 8.84 (d, 1H), 9.36 (t, 1H), 10.32 (s, 1H).

Example 24A 1-(5-Ethyl-1,3-thiazol-2-yl)acetone

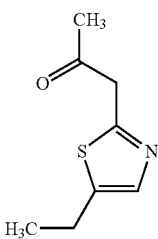

600 mg (4.72 mmol) of 5-ethyl-2-methyl-1,3-thiazole [M. Poite et al., *Bull. Chem. Soc. Fr.*, 2078-2085 (1962)] are dissolved in 20 ml of abs. THF and, at −78° C., 2.08 ml (5.18 mmol) of n-butyllithium (2.5 M solution in hexane) are added dropwise. After stirring at −78° C. for two hours, 706 mg (8.02 mmol) of ethyl acetate are added as a solution in 10 ml of abs. THF. The mixture is stirred at −78° C. for 1 h and then warmed to room temperature. It is then hydrolyzed with sodium bicarbonate solution, and the mixture is extracted three times with diethyl ether. The combined organic phases are dried with magnesium sulfate, and the solvent is removed in a rotary evaporator. The crude product is purified by MPLC (Biotage 40M cartridge, eluent: isohexane/ethyl acetate 80:20). 50 mg (6% of theory) of the title compound are obtained.

GC-MS (Method 2): $R_t$=4.42 min; MS (EIpos): m/z=169 $[M]^+$.

Example 25A

3-Methoxy-4-[2-(5-methyl-1,3,4-thiadiazol-2-yl)-3-oxobut-1-en-1-yl]benzonitrile

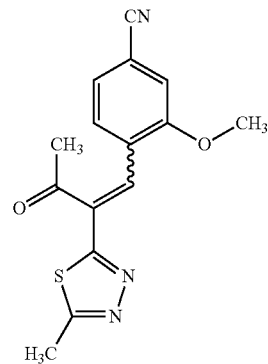 [SMILES: COc1cc(C#N)ccc1C=C(C(C)=O)c1nnc(C)s1]

1.34 g (8.32 mmol) of 1-(5-methyl-1,3,4-thiadiazol-2-yl) acetone [T. Saito et al., *J. Heterocycl. Chem.* 20, 73-75 (1983)] and 1.30 g (8.32 mmol) of the compound from example 3A are dissolved in 20 ml of dichloromethane, and 0.165 ml (1.66 mmol) of piperidine and 0.100 ml (1.66 mmol) of acetic acid are added. The reaction mixture is heated under reflux with an inverse water trap overnight. The volatile components are removed in a rotary evaporator, and the crude product is purified by column chromatography (silica gel; eluent: initially dichloromethane, then cyclohexane/ethyl acetate 4:1→1:1). 1.17 g (47% of theory) of the title compound are obtained as a mixture of the E/Z isomers which can be crystallized from ethyl acetate/n-pentane. 530 mg of the title compound are obtained as a crystalline solid in this way.

LC-MS (Method 1): $R_t$=1.97 min; MS (EIpos): m/z=300 $[M+H]^+$.

Exemplary Embodiments

Example 1

4-(4-Cyano-2-methoxyphenyl)-2,6-dimethyl-5-(4-methyl-1,3-thiazol-2-yl)-1,4-dihydropyridine-3-carbonitrile

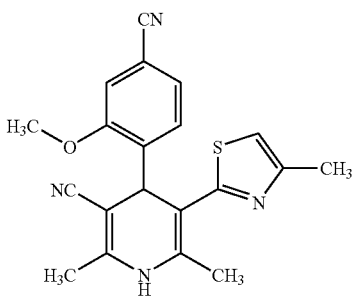

800 mg (4.96 mmol) of the compound from example 3A, 770 mg (4.96 mmol) of the compound from example 4A and 407 mg (4.96 mmol) of 3-aminocrotononitrile are dissolved in 12 ml of isopropanol and stirred at the reflux temperature overnight. After cooling to room temperature, the volatile components are removed in a rotary evaporator, and the crude product is taken up in 20 ml of ethyl acetate. After stirring at the reflux temperature for 60 min, the resulting solid is filtered off hot. The precipitate obtained in this way is washed with a little diethyl ether. 720 mg (40% of theory) of the title compound are obtained.

LC-MS (Method 3): $R_t$=2.15 min; (Elpos): m/z=363 [M+H]$^+$ $^1$H-NMR (300 MHz, DMSO-d$_6$): δ [ppm]=1.99 (s, 3H), 2.25 (s, 3H), 2.40 (s, 3H), 3.89 (s, 3H), 5.20 (s, 1H), 6.98 (s, 1H), 7.23 (d, 1H), 7.34 (d, 1H), 7.46 (s, 1H), 9.11 (s, 1H).

Example 2

4-(4-Cyano-2-methoxyphenyl)-6-ethyl-2-methyl-5-(4-methyl-1,3-thiazol-2-yl)-1,4-dihydropyridine-3-carbonitrile

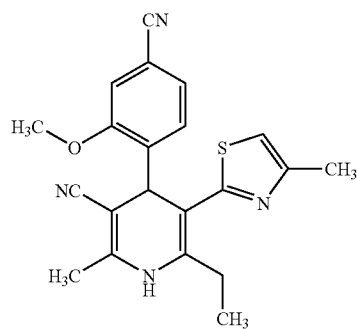

100 mg (0.620 mmol) of the compound from example 3A, 100 mg (0.310 mmol, 50% purity) of the compound from example 5A and 51 mg (0.620 mmol) of 3-aminocrotononitrile are dissolved in 4 ml of isopropanol and stirred at the reflux temperature overnight. After cooling to room temperature, the volatile components are removed in a rotary evaporator, and the crude product is purified by preparative HPLC (eluent: acetonitrile/water with 0.1% formic acid, gradient 20:80→95:5). 78 mg (66% of theory) of the title compound are obtained.

LC-MS (Method 3): $R_t$=2.32 min; (Elpos): m/z=377 [M+H]$^+$ $^1$H-NMR (300 MHz, DMSO-d$_6$): δ [ppm]=1.21 (t, 3H), 2.00 (s, 3H), 2.26 (s, 3H), 2.77 (m, 1H), 2.85 (m, 1H), 3.88 (s, 3H), 5.13 (s, 1H), 6.97 (s, 1H), 7.23 (d, 1H), 7.36 (dd, 1H), 7.47 (d, 1H), 9.07 (s, 1H).

Example 3

4-(4-Cyano-2-methoxyphenyl)-6-methyl-5-(4-methyl-1,3-thiazol-2-yl)-2-(trifluoromethyl)-1,4-dihydropyridine-3-carbonitrile

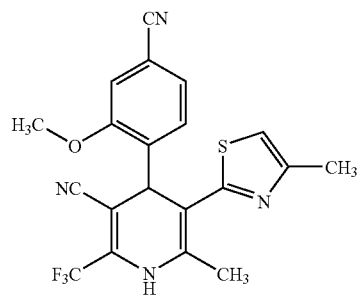

100 mg (0.335 mmol) of the compound from example 6A, 46 mg (0.335 mmol) of 3-amino-4,4,4-tri-fluorobut-2-enenitrile [preparation in analogy to U.S. Pat. No. 3,635,977 and K. Krespan, J. Org. Chem. 34, 42-45 (1969)] and 5.6 mg (0.05 mmol) of potassium tert-butoxide are dissolved in 4 ml of isopropanol and stirred at the reflux temperature overnight. After cooling to room temperature, the volatile components are removed in a rotary evaporator, and the crude product is purified by preparative HPLC (eluent: acetonitrile/water with 0.1% formic acid, gradient 20:80→95:5). 119 mg (82% of theory) of the title compound are obtained.

LC-MS (Method 3): $R_t$=2.40 min; (Elpos): m/z=417 [M+H]$^+$ $^1$H-NMR (300 MHz, DMSO-d$_6$): δ [ppm]=2.27 (s, 3H), 2.45 (s, 3H), 3.91 (s, 3H), 5.40 (s, 1H), 7.11 (s, 1H), 7.27 (d, 1H), 7.39 (dd, 1H), 7.53 (d, 1H), 9.90 (s, 1H).

Example 4

2,6-Dimethyl-4-(2-methyl-4-oxo-4H-chromen-8-yl)-5-(4-methyl-1,3-thiazol-2-yl)-1,4-dihydro-pyridine-3-carbonitrile

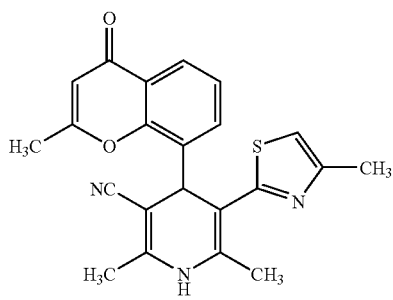

181 mg (0.97 mmol) of the compound from example 11A, 150 mg (0.97 mmol) of the compound from example 4A and 79 mg (0.97 mmol) of 3-aminocrotononitrile are dissolved in 4 ml of isopropanol and stirred at the reflux temperature overnight. After cooling to room temperature, the volatile components are removed in a rotary evaporator, the crude material is taken up in 5 ml of ethyl acetate, and the precipitated product is then filtered off 240 mg (64% of theory) of the title compound are obtained.

LC-MS (Method 1): $R_t$=2.09 min; (Elpos): m/z=390 [M+H]$^+$ $^1$H-NMR (300 MHz, DMSO-d$_6$): δ [ppm]=2.03 (s, 3H), 2.22 (s, 3H), 2.39 (s, 3H), 2.44 (s, 3H), 5.39 (s, 1H), 6.27 (s, 1H), 6.98 (d, 1H), 7.37 (t, 1H), 7.56 (dd, 1H), 7.86 (dd, 1H), 9.23 (s, 1H).

Example 5

4-(4-Cyano-2-methoxyphenyl)-2-methyl-5-(4-methyl-1,3-thiazol-2-yl)-6-propyl-1,4-dihydropyridine-3-carbonitrile

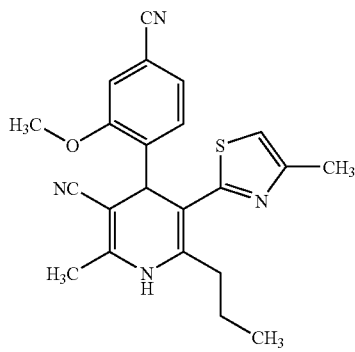

100 mg (0.620 mmol) of the compound from example 3A, 114 mg (0.620 mmol) of the compound from example 12A and 51 mg (0.620 mmol) of 3-aminocrotononitrile are dissolved in 4 ml of isopropanol and stirred at the reflux temperature overnight. After cooling to room temperature, the volatile components are removed in a rotary evaporator, and the crude product is purified by preparative HPLC (eluent: acetonitrile/water with 0.1% formic acid, gradient 20:80→95:5). 134 mg (66% of theory) of the title compound are obtained.

LC-MS (Method 4): $R_t$=3.86 min; (Elpos): m/z=391 [M+H]$^+$ $^1$H-NMR (300 MHz, DMSO-d$_6$): δ [ppm]=0.98 (t, 3H), 1.66 (m, 2H), 1.99 (s, 3H), 2.26 (s, 3H), 2.69 (m, 1H), 2.81 (m, 1H), 3.88 (s, 3H), 5.16 (s, 1H), 6.96 (d, 1H), 7.23 (d, 1H), 7.36 (dd, 1H), 7.46 (d, 1H), 9.05 (s, 1H).

Example 6

4-(2-Bromophenyl)-2,6-dimethyl-5-(4-methyl-1,3-thiazol-2-yl)-1,4-dihydropyridine-3-carbonitrile

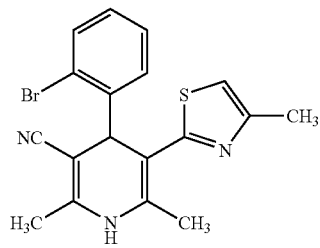

150 mg (0.811 mmol) of 2-bromobenzaldehyde, 126 mg (0.811 mmol) of the compound from example 4A and 67 mg (0.811 mmol) of 3-aminocrotononitrile are dissolved in 4 ml of isopropanol and stirred at the reflux temperature overnight. After cooling to room temperature, the volatile components are removed in a rotary evaporator, the crude material is taken up in 5 ml of ethyl acetate, and the precipitated product is then filtered off 190 mg (61% of theory) of the title compound are obtained.

LC-MS (Method 1): $R_t$=2.44 min; (Elpos): m/z=386 [M+H]$^+$ $^1$H-NMR (300 MHz, DMSO-d$_6$): δ [ppm]=2.01 (s, 3H), 2.26 (s, 3H), 2.36 (s, 3H), 5.22 (s, 1H), 7.00 (s, 1H), 7.11 (m, 1H), 7.32 (d, 2H), 7.53 (d, 1H), 9.13 (s, 1H).

Example 7

4-(2-Chloro-4-fluorophenyl)-2,6-dimethyl-5-(4-methyl-1,3-thiazol-2-yl)-1,4-dihydropyridine-3-carbonitrile

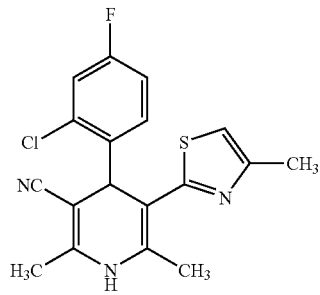

150 mg (0.946 mmol) of 2-chloro-4-fluorobenzaldehyde, 147 mg (0.811 mmol) of the compound from example 4A and 78 mg (0.811 mmol) of 3-aminocrotononitrile are dissolved in 4 ml of isopropanol and stirred at the reflux temperature overnight. After cooling to room temperature, the volatile components are removed in a rotary evaporator, the crude material is taken up in 5 ml of ethyl acetate, and the precipitated product is then filtered off 199 mg (58% of theory) of the title compound are obtained.

LC-MS (Method 1): $R_t$=2.50 min; (Elpos): m/z=360 [M+H]$^+$ $^1$H-NMR (300 MHz, DMSO-d$_6$): δ [ppm]=2.01 (s, 3H), 2.25 (s, 3H), 2.36 (s, 3H), 5.24 (s, 1H), 7.01 (s, 1H), 7.17 (dt, 1H), 7.31-7.38 (m, 2H), 9.16 (s, 1H).

Example 8

4-(4-Cyano-2-methoxyphenyl)-6-(methoxymethyl)-2-methyl-5-(4-methyl-1,3-thiazol-2-yl)-1,4-dihydropyridine-3-carbonitrile

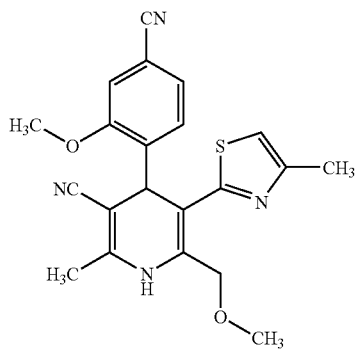

100 mg (0.305 mmol) of the compound from example 14A and 25 mg (0.305 mmol) of 3-amino-crotononitrile are dissolved in 3 ml of isopropanol and stirred at the reflux temperature overnight. After cooling to room temperature, the volatile components are removed in a rotary evaporator, and the crude product is purified by preparative HPLC (eluent: acetonitrile/water with 0.1% formic acid, gradient 20:80→95:5). 59 mg (49% of theory) of the title compound are obtained.

LC-MS (Method 1): R$_t$=2.37 min; (Elpos): m/z=393 [M+H]$^+$ $^1$H-NMR (300 MHz, DMSO-d$_6$): δ [ppm]=2.03 (s, 3H), 2.28 (s, 3H), 3.35 (s, 3H), 3.88 (s, 3H), 4.59 (d, 1H), 4.63 (d, 1H), 5.18 (s, 1H), 7.03 (s, 1H), 7.26 (d, 1H), 7.38 (dd, 1H), 7.49 (d, 1H), 9.10 (s, 1H).

Example 9

4-(4-Cyano-2-methoxyphenyl)-6-(methoxymethyl)-5-(4-methyl-1,3-thiazol-2-yl)-2-(trifluoromethyl)-1,4-dihydropyridine-3-carbonitrile

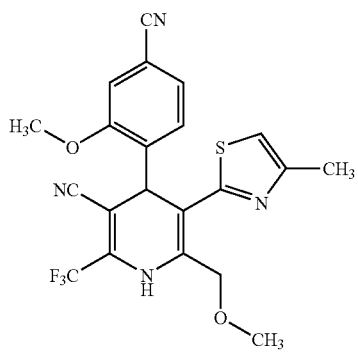

100 mg (0.305 mmol) of the compound from example 14A, 41 mg (0.335 mmol) of 3-amino-4,4,4-trifluorobut-2-enenitrile [preparation in analogy to U.S. Pat. No. 3,635,977 and K. Krespan, J. Org. Chem. 34, 42-45 (1969)] and 5.1 mg (0.05 mmol) of potassium tert-butoxide are dissolved in 4 ml of isopropanol and stirred at the reflux temperature overnight. After cooling to room temperature, the volatile components are removed in a rotary evaporator, and the crude material is purified by preparative HPLC (eluent: acetonitrile/water with 0.1% formic acid, gradient 20:80→95:5). 18 mg (13% of theory) of the title compound are obtained.

LC-MS (Method 1): R$_t$=2.62 min; (Elpos): m/z=447 [M+H]$^+$ $^1$H-NMR (300 MHz, DMSO-d$_6$): δ [ppm]=2.29 (s, 3H), 3.34 (s, 3H), 3.90 (s, 3H), 4.51 (d, 1H), 4.60 (d, 1H), 5.40 (s, 1H), 7.17 (s, 1H), 7.29 (d, 1H), 7.42 (dd, 1H), 7.55 (d, 1H), 9.97 (s, 1H).

Example 10

4-(4-Cyano-2-methoxyphenyl)-6-ethyl-5-(4-methyl-1,3-thiazol-2-yl)-2-(trifluoromethyl)-1,4-dihydropyridine-3-carbonitrile

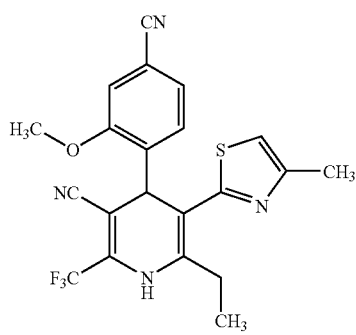

150 mg (0.480 mmol) of the compound from example 20A, 65 mg (0.480 mmol) of 3-amino-4,4,4-trifluorobut-2-enenitrile [preparation in analogy to U.S. Pat. No. 3,635,977 and K. Krespan, J. Org. Chem. 34, 42-45 (1969)] and 8.1 mg (0.072 mmol) of potassium tert-butoxide are dissolved in 4 ml of isopropanol and stirred at the reflux temperature overnight. After cooling to room temperature, the volatile components are removed in a rotary evaporator, and the crude material is purified initially by preparative HPLC (eluent: acetonitrile/water with 0.1% formic acid, gradient 20:80→95:5) and then by MPLC (Biotage 12M cartridge, eluent: isohexane/ethyl acetate 80:20). 25 mg (12% of theory) of the title compound are obtained.

LC-MS (Method 1): R$_t$=2.68 min; (Elpos): m/z=431 [M+H]$^+$ $^1$H-NMR (300 MHz, DMSO-d$_6$): δ [ppm]=1.21 (t, 3H), 2.28 (s, 3H), 2.85 (d, 1H), 2.89 (d, 1H), 3.90 (s, 3H), 5.32 (s, 1H), 7.10 (s, 1H), 7.25 (d, 1H), 7.41 (dd, 1H), 7.54 (d, 1H), 9.89 (s, 1H).

Example 11

4-(4-Cyano-2-methoxyphenyl)-5-(4-ethyl-1,3-thiazol-2-yl)-2,6-dimethyl-1,4-dihydropyridine-3-carbonitrile

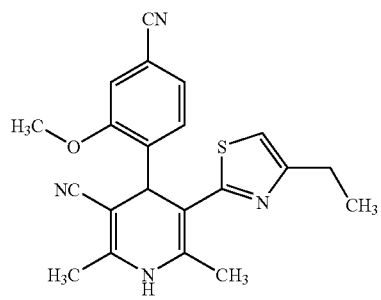

770 mg (4.78 mmol) of the compound from example 3A and 890 mg (5.26 mmol) of the compound from example 17A are dissolved in 15 ml of dichloromethane, and 0.473 ml (4.78 mmol) of piperidine and 0.247 ml (4.78 mmol) of acetic acid are added. The reaction mixture is heated under reflux with an inverse water trap overnight. The volatile components are removed in a rotary evaporator, and the crude product is purified by MPLC (Biotage 12M cartridge, eluent: isohexane/ ethyl acetate 80:20→70:30). 920 mg (66% of theory) of 4-[2-(4-ethyl-1,3-thiazol-2-yl)-3-oxobut-1-en-1-yl]-3-methoxybenzonitrile are obtained as a mixture of the E/Z isomers {LC-MS (Method 1): R$_t$=2.39 min; (Elpos): m/z=313 [M+H]$^+$} and without further working up.

150 mg (0.480 mmol) of the benzylidene compound obtained in this way and 39 mg (0.480 mmol) of 3-aminocrotononitrile are dissolved in 4 ml of isopropanol and stirred at the reflux temperature overnight. After cooling to room temperature, the volatile components are removed in a rotary evaporator, and the crude material is purified by preparative HPLC (eluent: acetonitrile/water with 0.1% formic acid, gradient 20:80→95:5). 26 mg (14% of theory) of the title compound are obtained.

LC-MS (Method 4): R$_t$=3.66 min; (Elpos): m/z=377 [M+H]$^+$ $^1$H-NMR (300 MHz, DMSO-d$_6$): δ [ppm]=1.12 (t, 3H), 1.99 (s, 3H), 2.40 (s, 3H), 2.59 (q, 2H). 3.89 (s, 3H), 5.22 (s, 1H), 6.98 (s, 1H), 7.24 (d, 1H), 7.34 (dd, 1H), 7.47 (d, 1H), 9.12 (s, 1H).

Example 12

5-(1,3-Benzothiazol-2-yl)-4-(4-cyano-2-methoxyphenyl)-2,6-dimethyl-1,4-dihydropyridine-3-carbonitrile

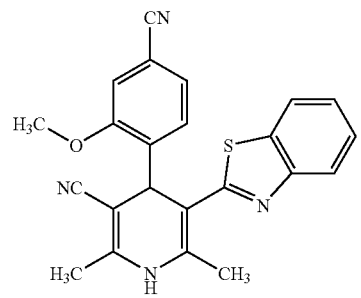

150 mg (0.931 mmol) of the compound from example 3A, 178 mg (0.931 mmol) of 1-(1,3-benzo-thiazol-2-yl)acetone [Costa et al., J. Heterocycl. Chem. 28, 1541-1544 (1991)] and 76 mg (0.931 mmol) of 3-aminocrotononitrile are dissolved in 6 ml of isopropanol and stirred at the reflux temperature overnight. After cooling to room temperature, the volatile components are removed in a rotary evaporator. The crude product obtained in this way is recrystallized from acetonitrile. 40 mg (11% of theory) of the title compound are obtained.

LC-MS (Method 4): R$_t$=3.78 min; (Elpos): m/z=399 [M+H]$^+$ $^1$H-NMR (300 MHz, DMSO-d$_6$): δ [ppm]=2.02 (s, 3H), 2.53 (s, 3H), 3.94 (s, 3H), 5.33 (s, 1H), 7.26-7.32 (m, 2H), 7.35 (dd, 1H), 7.41 (dt, 1H), 7.50 (d, 1H), 7.79 (d, 1H), 7.94 (d, 1H), 9.36 (s, 1H).

Example 13

4-(2,4-Dichlorophenyl)-2,6-dimethyl-5-(4-methyl-1,3-thiazol-2-yl)-1,4-dihydropyridine-3-carbonitrile

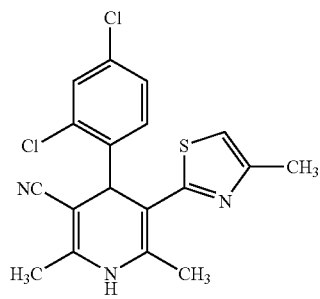

150 mg (0.857 mmol) of 2,4-dichlorobenzaldehyde, 133 mg (0.857 mmol) of the compound from example 4A and 70 mg (0.857 mmol) of 3-aminocrotononitrile are dissolved in 4 ml of isopropanol and stirred at the reflux temperature overnight. After cooling to room temperature, the volatile components are removed in a rotary evaporator, and the crude product is taken up in 3 ml of ethyl acetate. The crystallizing solid is removed by filtration. The product obtained in this way is washed with a little diethyl ether. 85 mg (26% of theory) of the title compound are obtained.

LC-MS (Method 8): $R_t$=3.74 min; (Elpos): m/z=376 [M+H]$^+$ $^1$H-NMR (300 MHz, DMSO-d$_6$): δ [ppm]=2.01 (s, 3H), 2.25 (s, 3H), 2.35 (s, 3H), 5.26 (s, 1H), 7.02 (d, 1H), 7.32 (d, 1H), 7.37 (dd, 1H), 7.53 (d, 1H), 9.18 (s, 1H).

Example 14

4-(2-Bromo-4-fluorophenyl)-2,6-dimethyl-5-(4-methyl-1,3-thiazol-2-yl)-1,4-dihydropyridine-3-carbonitrile

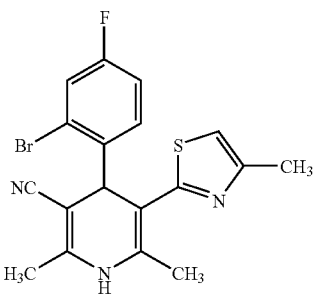

150 mg (0.739 mmol) of 2-bromo-4-fluorobenzaldehyde, 115 mg (0.739 mmol) of the compound from example 4A and 61 mg (0.739 mmol) of 3-aminocrotononitrile are dissolved in 4 ml of isopropanol and stirred at the reflux temperature overnight. After cooling to room temperature, the volatile components are removed in a rotary evaporator, and the crude product is purified by flash chromatography (silica gel, mobile phase: cyclohexane/ethyl acetate 1:1). After removal of the solvent, the product is obtained by crystallization from diisopropyl ether. Drying under high vacuum results in 91 mg (30% of theory) of the title compound.

LC-MS (Method 3): $R_t$=2.39 min; (Elpos): m/z=405 [M+H]$^+$ $^1$H-NMR (300 MHz, DMSO-d$_6$): δ [ppm]=2.01 (s, 3H), 2.26 (s, 3H), 2.35 (s, 3H), 5.22 (s, 1H), 7.02 (d, 1H), 7.21 (dt, 1H), 7.34 (dd, 1H), 7.48 (dd, 1H), 9.16 (s, 1H).

Example 15

4-(4-Cyano-2-methoxyphenyl)-2,6-dimethyl-5-(4,5,6,7-tetrahydro-1,3-benzothiazol-2-yl)-1,4-dihydropyridine-3-carbonitrile

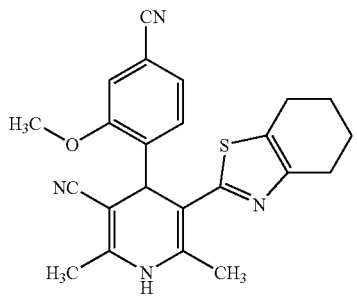

150 mg (0.931 mmol) of the compound from example 3A, 181 mg (0.931 mmol) of the compound from example 19A and 76 mg (0.931 mmol) of 3-aminocrotononitrile are dissolved in 4 ml of isopropanol and stirred at the reflux temperature overnight. After cooling to room temperature, the volatile components are removed in a rotary evaporator, and the crude product is taken up in 3 ml of ethyl acetate. The crystallizing solid is removed by filtration. The precipitate obtained in this way is washed with hot acetonitrile and dried under high vacuum. 131 mg (35% of theory) of the title compound are obtained.

LC-MS (Method 3): $R_t$=2.43 min; (Elpos): m/z=403 [M+H]$^+$ $^1$H-NMR (300 MHz, DMSO-d$_6$): δ [ppm]=1.71 (m, 4H), 1.98 (s, 3H), 2.37 (s, 3H), 2.57 (m, 2H), 2.62 (m, 2H), 3.89 (s, 3H), 5.16 (s, 1H), 7.20 (d, 1H), 7.35 (dd, 1H), 7.47 (d, 1H), 9.09 (s, 1H).

Example 16

4-(4-Fluoro-2-methoxyphenyl)-2,6-dimethyl-5-(4-methyl-1,3-thiazol-2-yl)-1,4-dihydropyridine-3-carbonitrile

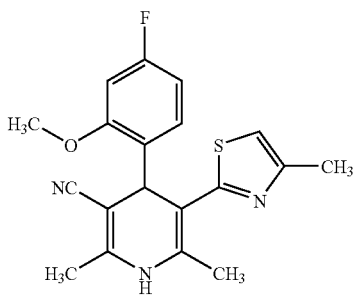

150 mg (0.973 mmol) of 4-fluoro-2-methoxybenzaldehyde, 151 mg (0.973 mmol) of the compound from example 4A and 80 mg (0.973 mmol) of 3-aminocrotononitrile are dissolved in 4 ml of isopropanol and stirred at the reflux temperature overnight. After cooling to room temperature, the volatile components are removed in a rotary evaporator, and the crude product is purified by flash chromatography (silica gel, mobile phase: cyclohexane/ethyl acetate 1:1). After removal of the solvent, the product is obtained by crystallization from diisopropyl ether. Drying under high vacuum results in 123 mg (36% of theory) of the title compound.

LC-MS (Method 1): $R_t$=2.43 min; (Elpos): m/z=356 [M+H]$^+$ $^1$H-NMR (300 MHz, DMSO-$d_6$): δ [ppm]=1.97 (s, 3H), 2.26 (s, 3H), 2.39 (s, 3H), 3.83 (s, 3H), 5.04 (s, 1H), 6.68 (dt, 1H), 6.87 (dd, 1H), 6.95 (s, 1H), 7.07 (dd, 1H), 9.00 (s, 1H).

Example 17

2-Methoxy-2',6'-dimethyl-5'-(4-methyl-1,3-thiazol-2-yl)-1',4'-dihydro-3,4'-bipyridine-3'-carbonitrile

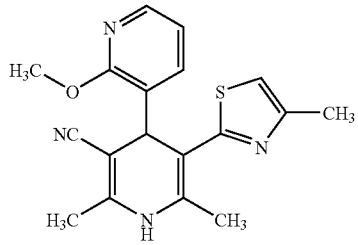

150 mg (1.09 mmol) of 2-methoxy-3-pyridinecarboxaldehyde, 170 mg (1.09 mmol) of the compound from example 4A and 90 mg (1.09 mmol) of 3-aminocrotononitrile are dissolved in 4 ml of isopropanol and stirred at the reflux temperature overnight. After cooling to room temperature, the volatile components are removed in a rotary evaporator, and the crude product is taken up in 3 ml of ethyl acetate. The crystallizing solid is removed by filtration. The precipitate obtained in this way is washed with a little diethyl ether. 216 mg (58% of theory) of the title compound are obtained.

LC-MS (Method 8): $R_t$=2.87 min; (Elpos): m/z=339 [M+H]$^+$ $^1$H-NMR (300 MHz, DMSO-$d_6$): δ [ppm]=2.00 (s, 3H), 2.26 (s, 3H), 2.39 (s, 3H), 3.90 (s, 3H), 5.02 (s, 1H), 6.91 (m, 1H), 6.98 (s, 1H), 7.40 (d, 1H), 7.99 (m, 1H), 9.09 (s, 1H).

Example 18

2,6-Dimethyl-4-(3-methylquinolin-5-yl)-5-(4-methyl-1,3-thiazol-2-yl)-1,4-dihydropyridine-3-carbonitrile

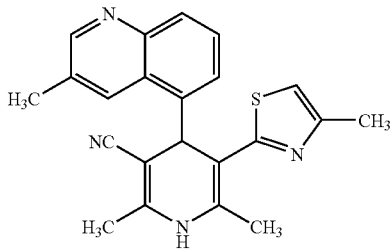

150 mg (0.876 mmol) of the compound from example 23A, 135 mg (0.876 mmol) of the compound from example 4A and 71 mg (0.876 mmol) of 3-aminocrotononitrile are dissolved in 4 ml of isopropanol and stirred at the reflux temperature overnight. After cooling to room temperature, the volatile components are removed in a rotary evaporator, and the crude product is purified by preparative HPLC (eluent: acetonitrile/water with 0.1% formic acid, gradient 20:80→95:5). 145 mg (44% of theory) of the title compound are obtained.

LC-MS (Method 8): $R_t$=2.23 min; (Elpos): m/z=373 [M+H]$^+$ $^1$H-NMR (300 MHz, DMSO-$d_6$): δ [ppm]=2.02 (s, 3H), 2.17 (s, 3H), 2.40 (s, 3H), 5.64 (s, 1H), 6.89 (d, 1H), 7.47 (dd, 1H), 7.61 (t, 1H), 7.82 (d, 1H), 8.72 (s, 1H), 8.77 (d, 1H), 9.18 (s, 1H) (1 CH$_3$ signal overlapped by solvent signal).

Example 19

4-(4-Fluoro-1-naphthyl)-2,6-dimethyl-5-(4-methyl-1,3-thiazol-2-yl)-1,4-dihydropyridine-3-carbonitrile

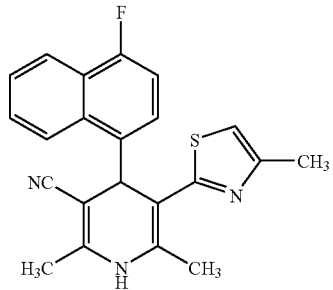

150 mg (0.861 mmol) of 4-fluoro-1-naphthaldehyde, 134 mg (0.861 mmol) of the compound from example 4A and 70 mg (0.861 mmol) of 3-aminocrotononitrile are dissolved in 4 ml of isopropanol and stirred at the reflux temperature overnight. After cooling to room temperature, the volatile components are removed in a rotary evaporator, and the crude product is purified by preparative HPLC (eluent: acetonitrile/water with 0.1% formic acid, gradient 20:80→95:5). 14 mg (4% of theory) of the title compound are obtained.

LC-MS (Method 1): $R_t$=2.64 min; (Elpos): m/z=376 [M+H]$^+$ $^1$H-NMR (300 MHz, DMSO-$d_6$): δ [ppm]=2.01 (s, 3H), 2.17 (s, 3H), 2.41 (s, 3H), 5.62 (s, 1H), 6.87 (s, 1H), 7.28 (dd, 1H), 7.39 (dd, 1H), 7.64 (t, 1H), 7.70 (dt, 1H), 8.04 (d, 1H), 8.58 (d, 1H), 9.16 (s, 1H).

Example 20

4-(2-Cyano-4-fluorophenyl)-2,6-dimethyl-5-(4-methyl-1,3-thiazol-2-yl)-1,4-dihydropyridine-3-carbonitrile

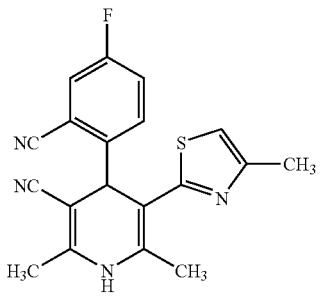

50 mg (0.124 mmol) of the compound from example 14 and 10.7 mg (0.092 mmol) of zinc cyanide in 0.5 ml of abs. DMF are mixed with 4.7 mg (0.004 mmol) of tetrakis(triphenyl-phosphine)palladium(0) and reacted in a single mode microwave (Emrys Optimizer) at 220° C. for 5 min. After the reaction has taken place (TLC check), the reaction mixture is purified directly by preparative HPLC (eluent: acetonitrile/water with 0.1% formic acid, gradient 20:80→95:5). 24 mg (55% of theory) of the title compound are obtained.

LC-MS (Method 4): $R_t$=3.47 min; (Elpos): m/z=351 [M+H]$^+$ $^1$H-NMR (300 MHz, DMSO-$d_6$): δ [ppm]=2.04 (s, 3H), 2.24 (s, 3H), 2.31 (s, 3H), 5.21 (s, 1H), 7.06 (d, 1H), 7.44-7.55 (m, 2H), 7.76 (dd, 1H), 9.28 (s, 1H).

Example 21 ent-4-(4-Cyano-2-methoxyphenyl)-2,6-dimethyl-5-(4-methyl-1,3-thiazol-2-yl)-1,4-dihydropyridine-3-carbonitrile [(−)-enantiomer and (+)-enantiomer]

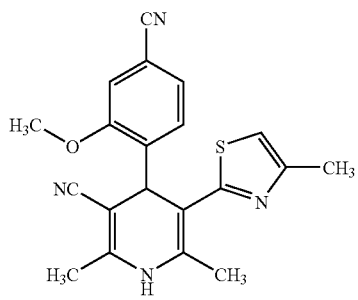

The racemate from example 1 is fractionated into its antipodes by chiral phase chromatography [column: 680 mm×40 mm; chiral silica gel phase based on the selector poly(N-methacryloyl-D-leucine tert-butylamide); eluent: isohexane/ethyl acetate 55:45 (v/v); temperature: 24° C.; flow rate: 80 ml/min; UV detection: 260 nm].

The retention times from a comparable analytical HPLC based on the same selector [column: 250 mm×4.6 mm; eluent: isohexane/ethyl acetate 4:1 (v/v); flow rate: 1 ml/min] and the specific rotations of the enantiopure compounds were determined to be as follows:

(−) Enantiomer:

$R_t$=7.01 min; ee~97% specific rotation (chloroform, 589 nm, 20° C., c=0.50500 g/100 ml): −578.2°.

(+) Enantiomer:

$R_t$=7.61 min; ee~96% specific rotation (chloroform, 589 nm, 20° C., c=0.50000 g/100 ml): +590.3°.

Example 22 ent-4-(4-Cyano-2-methoxyphenyl)-6-(methoxymethyl)-5-(4-methyl-1,3-thiazol-2-yl)-2-(trifluoromethyl)-1,4-dihydropyridine-3-carbonitrile [(−)-enantiomer and (+)-enantiomer]

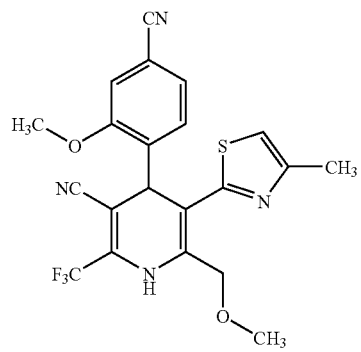

The racemate from example 9 is fractionated into its antipodes by chiral phase chromatography [column: 680 mm×40 mm; chiral silica gel phase based on the selector poly(N-methacryloyl-D-leucine tert-butylamide); eluent: isohexane/ethyl acetate 90:10 (v/v); temperature: 24° C.; flow rate: 80 ml/min; UV detection: 260 nm].

The retention times from a comparable analytical HPLC based on the same selector [column: 250 mm×4.6 mm; eluent: isohexane/ethyl acetate 10:1 (v/v); flow rate: 2 ml/min] and the specific rotations of the enantiopure compounds were determined to be as follows:

(−) Enantiomer:

$R_t$=10.07 min; ee=98% specific rotation (chloroform, 589 nm, 20° C., c=0.49500 g/100 ml): −759.1°.

(+) Enantiomer:

$R_t$=13.66 min; ee=98.5% specific rotation (chloroform, 589 nm, 20° C., c=0.50000 g/100 ml): +757.2°.

Example 23

4-(4-Cyano-2-methoxyphenyl)-5-(5-ethyl-1,3-thiazol-2-yl)-2,6-dimethyl-1,4-dihydropyridine-3-carbonitrile

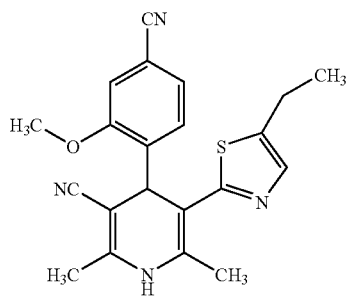

47.6 mg (0.295 mmol) of the compound from example 3A, 50 mg (0.295 mmol) of the compound from example 24A and 24 mg (0.295 mmol) of 3-aminocrotononitrile are dissolved in 2 ml of isopropanol and stirred at the reflux temperature overnight. After cooling to room temperature, the volatile components are removed in a rotary evaporator, and the crude product is purified by preparative HPLC (eluent: acetonitrile/water with 0.1% formic acid, gradient 20:80→95:5). 23 mg (19% of theory) of the title compound are obtained in 90% purity (by LC-MS) and can be further purified by crystallization from ethyl acetate. 3 mg (3% of theory) of the target compound are thus isolated in pure form.

LC-MS (Method 8): $R_t$=3.39 min; (Elpos): m/z=377 [M+H]$^+$ $^1$H-NMR (300 MHz, DMSO-d$_6$): δ [ppm]=1.15 (t, 3H), 1.98 (s, 3H), 2.36 (s, 3H), 2.72 (q, 2H), 3.88 (s, 3H), 5.20 (s, 1H), 7.19 (d, 1H), 7.33 (dd, 1H), 7.35 (br. s, 1H), 7.47 (d, 1H), 9.11 (s, 1H).

Example 24

4-(4-Cyano-2-methoxyphenyl)-2,6-dimethyl-5-(5-methyl-1,3,4-thiadiazol-2-yl)-1,4-dihydropyridine-3-carbonitrile

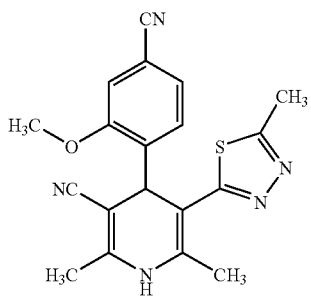

150 mg (0.501 mmol) of the compound from example 25A and 41 mg (0.501 mmol) of 3-amino-crotononitrile are dissolved in 5 ml of isopropanol and stirred at the reflux temperature overnight. After cooling to room temperature, the volatile components are removed in a rotary evaporator, and the crude product is purified by preparative HPLC (eluent: acetonitrile/water with 0.1% formic acid, gradient 20:80→95:5). Crystallization from ethyl acetate/diethyl ether results in 30 mg (16% of theory) of the title compound.

LC-MS (Method 8): $R_t$=2.62 min; (Elpos): m/z=364 [M+H]$^+$ $^1$H-NMR (300 MHz, DMSO-d$_6$): δ [ppm]=2.00 (s, 3H), 2.30 (s, 3H), 2.59 (s, 3H), 3.87 (s, 3H), 5.18 (s, 1H), 7.25 (d, 1H), 7.36 (dd, 1H), 7.49 (d, 1H), 9.28 (s, 1H).

B. ASSESSMENT OF THE PHARMACOLOGICAL ACTIVITY

Abbreviations:

| | |
|---|---|
| DMEM | Dulbecco's modified Eagle medium |
| DNA | deoxyribonucleic acid |
| FCS | fetal calf serum |
| HEPES | 4-(2-hydroxyethyl)-1-piperazineethanesulfonic acid |
| PCR | polymerase chain reaction |
| Tris | tris(hydroxymethyl)methylamine |

The advantageous pharmacological properties of the compounds of the invention can be shown in the following assays:

1. Cellular In Vitro Assay to Determine the Inhibitory MR Activity and MR Selectivity Compared with Other Steroid Hormone Receptors Antagonists of the human mineralocorticoid receptor (MR) are identified, and the activity of the compounds described herein is quantified with the aid of a recombinant cell line. The cell is originally derived from a hamster ovary epithelial cell (Chinese Hamster Ovary, CHO K1, ATCC: American Type Culture Collection, Va. 20108, USA).

An established chimera system in which the ligand-binding domains of human steroid hormone receptors are fused to the DNA-binding domain of the yeast transcription factor GAL4 is used in this CHO K1 cell line. The GAL4-steroid hormone receptor chimeras produced in this way are cotransfected and stably expressed with a reporter construct in the CHO cells.

Clonings:

To generate the GAL4-steroid hormone receptor chimeras, the GAL4 DNA binding domain (amino acids 1-147) from the vector pFC2-dbd (from Stratagene) is cloned with the PCR-amplified ligand-binding domains of the mineralocorticoid receptor (MR, amino acids 734-985), of the glucocorticoid receptor (GR, amino acids 443-777), of the progesterone receptor (PR, amino acids 680-933) and of the androgen receptor (AR, amino acids 667-919) into the vector pIRES2 (from Clontech). The reporter construct, which comprises five copies of the GAL4 binding site upstream of a thymidine kinase promoter, leads to expression of firefly-luciferase (*Photinus pyralis*) after activation and binding of the GAL4-steroid hormone receptor chimeras by the respective specific agonists aldosterone (MR), dexamethasone (GR), progesterone (PR) and dihydrotestosterone (AR).

Assay Procedure:

The MR, GR, PR and AR cells are plated out in medium (Optimem, 2.5% FCS, 2 mM glutamine, 10 mM HEPES) in 96- (or 384- or 1536-) well microtiter plates on the day before the assay and are kept in a cell incubator (96% humidity, 5% v/v CO$_2$, 37° C.). On the day of the assay, the substances to be tested are taken up in the abovementioned medium and added to the cells. About 10 to 30 minutes after addition of the test substances, the respective specific agonists of the steroid hormone receptors are added. After a further incubation time of 5 to 6 hours, the luciferase activity is measured with the aid of a video camera. The measured relative light units as a function of the substance concentration result in a sigmoidal stimulation curve. The $IC_{50}$ values are calculated with the aid of the GraphPad PRISM computer program (Version 3.02).

Table A shows the $IC_{50}$ values (MR) of representative exemplary compounds:

TABLE A

| Example No. | MR $IC_{50}$ [nM] |
|---|---|
| 1 | 94 |
| 3 | 10 |
| 4 | 95 |
| 12 | 74 |
| 18 | 278 |
| 23 | 18 |
| 24 | 320 |

2. In Vitro Assay to Determine Possible Binding Activity to the L-Type Calcium Channel Membrane preparations of the cerebral cortex of Wistar rats serve as starting material for a radioactive binding assay which is described in detail in the literature as standard assay [Ehlert, F. J., Roeske, W. R., Itoga E., Yamamura, H. I., *Life Sci.* 30, 2191-2202 (1982); Gould, R. J., Murphy, K. M. M., Snyder, S. H., *Proc. Natl. Acad. Sci. U.S.A.* 79, 3656-3660] and is used in contract investigations by commercial service suppliers (e.g. MDS Pharma Services). In this binding assay, serial dilutions of the test compounds in DMSO are incubated with the membrane preparations and the tritium-labeled ligand nitrendipine (0.1 nM) in a 50 mM TrisHCl buffer, pH 7.7, at 25° C. typically for 90 minutes, and the specific binding of the test compounds is determined by quantifying the specifically displaced, radiolabeled ligand. $IC_{50}$ values are determined by a nonlinear regression analysis.

The $IC_{50}$ value determined in this L-type calcium channel binding assay for a conventional calcium antagonist of the dihydropyridine type such as, for example, nitrendipine is 0.3 nM, whereas the $IC_{50}$ values for investigated examples of the compounds of the invention described herein are >1 µM and thus the affinity shown for the L-type calcium channel is reduced by a factor of at least 3000. Compounds with such a reduced residual binding affinity for the L-type calcium channel generally no longer show pronounced hemodynamic effects mediated by the L-type calcium channel in vivo.

3. In Vitro Assay for Functional Characterization of Possible Calcium Channel-Agonistic or -Antagonistic Effects of Test Compounds: Potassium Chloride-Induced Stimulation of the Isolated Rabbit Aorta The freshly isolated thoracic aorta of male New Zealand white rabbits is removed and cleaned of surrounding tissue. Then aortic rings with a length of 2 mm are put under an initial tension of 4 g in 10 ml organ baths with Krebs-Henseleit solution at 37° C. Contractions are induced by 40 mM KCl (submaximal contraction) and 15 mM KCl (minimal contraction) four times at an interval of 45 minutes in order to train the vessels and generate a stable resting tension. Each contraction is followed by a series of eleven rinsing cycles and a resting period of 30 minutes with previous retensioning. After the four pre-runs, the test substances are added to the organ baths in each case at the start of the resting period without further retensioning. The concentration of the test substances is increased by a factor of 10 for each of the four following contractions. To calculate the effect, the difference between the baseline tension and the value for the fourth pre-run contraction is set equal to 100%, and the following contraction peaks are related to this value. This experimental procedure makes it possible to differentiate calcium-agonistic (slight increase at the submaximal contraction, greater increase at the minimal contraction) and calcium-antagonistic effect of the substance (reduction at the submaximal contraction, greater reduction at the minimal contraction).

The $IC_{50}$ measured for a classical calcium antagonist of the dihydropyridine type such as, for example, nifedipine in this functional assay on an isolated organ is from 0.1 nM to 0.4 nM, whereas the $IC_{50}$ values for investigated examples of the compounds of the invention described herein are >1 µM, and thus the affinity shown for the L-type calcium channel is reduced by a factor of at least 2500. Compounds with such a low residual binding affinity for the L-type calcium channel no longer show pronounced hemodynamic effects mediated by the L-type calcium channel in vivo.

4. In Vivo Assay for Detecting the Cardiovascular Effect: Diuresis Investigations on Conscious Rats in Metabolism Cages Wistar rats (body weight 250-350 g) are kept with free access to feed (Altromin) and drinking water. From about 72 hours before the start of the test, the animals receive instead of the normal feed exclusively salt-reduced feed with a sodium chloride content of 0.02% (ssniff R/M-H, 10 mm with 0.02% Na, S0602-E081, ssniff Spezialdiaten GmbH, D-59494 Soest). During the test, the animals are housed singly in metabolism cages suitable for rats of this weight class (from Tecniplast Deutschland GmbH, D-82383 Hohenpeilβenberg) with free access to salt-reduced feed and drinking water for about 24 hours. At the start of the test, the substance to be tested is administered into the stomach of the animals by means of gavage in a volume of 0.5 ml/kg of body weight of a suitable solvent. Control animals receive only solvent. Controls and substance tests are carried out in parallel on the same day. Control groups and substance-dose groups each consist of 3 to 6 animals. During the test, the urine excreted by the animals is continuously collected in a receiver on the base of the cage. The urine volume per unit time is determined separately for each animal, and the concentration of the sodium and potassium ions excreted in the urine is measured by standard methods of flame photometry. The sodium/potassium ratio is calculated from the measurements as a measure of the effect of the substance. The measurement intervals are typically the period up to 8 hours after the start of the test (day interval) and the period from 8 to 24 hours after the start of the test (night interval). In a modified test design, the urine is collected and measured at intervals of two hours during the day interval. In order to obtain a sufficient amount of urine for this purpose, the animals receive a defined amount of water by gavage at the start of the test and then at intervals of two hours.

5. DOCA/Salt Model

Administration of deoxycorticosterone acetate (DOCA) in combination with a high-salt diet and unilateral kidney removal in rats induces hypertension which is characterized by relatively low renin levels. As a consequence of this endocrine hypertension (DOCA is a direct precursor of aldosterone), there is, depending on the chosen DOCA concentration, cardiac hypertrophy and further end organ damage, e.g. of the kidney, which is characterized inter alia by proteinuria and glomerulosclerosis. It is thus possible to investigate test substances in this rat model for the presence of an antihypertrophic and end organ-protecting effect.

Approximately 8-week old (body weight between 250 and 300 grams) male Sprague-Dawley (SD) rats undergo left uninephrectomy. For this purpose, the rats are anesthetized with 1.5-2% isoflurane in a mixture of 66% $N_2O$ and 33% $O_2$, and the kidney is removed through a flank incision. So-called sham-operated animals from which no kidney is removed serve as later control animals.

Uninephrectomized SD rats receive 1% sodium chloride in the drinking water and a subcutaneous injection of deoxycorticosterone acetate (dissolved in sesame oil; from Sigma) injected between the shoulder blades once a week (high dose: 100 mg/kg/week s.c.; normal dose: 30 mg/kg/week s.c.).

The substances which are to be investigated for their protective effect in vivo are administered by gavage or via the feed (from Ssniff). One day before the start of the test, the animals are randomized and assigned to groups with an identical number of animals, usually n=10, Throughout the test, drinking water and feed are available ad libitum to the animals. The substances are administered via the feed or once a day by gavage for 4-8 weeks. Animals serving as placebo group are treated in the same way but receive either only the solvent or the feed without test substance.

The effect of the test substances is determined by measuring hemodynamic parameters [blood pressure, heart rate, inotropism (dp/dt), relaxation time (tau), maximum left ventricular pressure, left-ventricular end-diastolic pressure (LVEDP)], determining the weight of the heart, kidney and lung, measuring the protein excretion, and by measuring gene expression of biomarkers (e.g. ANP, atrial natriuretic peptide, and BNP, brain natriuretic peptide) by means of RT/TaqMan PCR after RNA isolation from cardiac tissue.

Statistical analysis takes place using Student's t test after previous examination of the variances for homogeneity.

C. EXEMPLARY EMBODIMENTS OF PHARMACEUTICAL COMPOSITIONS

The compounds of the invention can be converted into pharmaceutical preparations in the following ways:

Tablet:

Composition:

100 mg of the compound of the invention, 50 mg of lactose (monohydrate), 50 mg of corn starch (native), 10 mg of polyvinylpyrrolidone (PVP 25) (from BASF, Ludwigshafen, Germany) and 2 mg of magnesium stearate.

Tablet weight 212 mg, diameter 8 mm, radius of curvature 12 mm.

Production:

The mixture of compound of the invention, lactose and starch is granulated with a 5% strength solution (m/m) of the PVP in water. The granules are mixed with the magnesium stearate for 5 minutes after drying. This mixture is compressed with a conventional tablet press (see above for format of the tablet). A guideline compressive force for the compression is 15 kN.

Suspension which can be Administered Orally:

Composition:

1000 mg of the compound of the invention, 1000 mg of ethanol (96%), 400 mg of Rhodigel® (xanthan gum from FMC, Pennsylvania, USA) and 99 g of water.

10 ml of oral suspension correspond to a single dose of 100 mg of the compound of the invention.

Production:

The Rhodigel is suspended in ethanol, and the compound of the invention is added to the suspension. The water is added while stirring. The mixture is stirred for about 6 h until the swelling of the Rhodigel is complete.

Solution which can be Administered Orally:

Composition:

500 mg of the compound of the invention, 2.5 g of polysorbate and 97 g of polyethylene glycol 400. 20 g of oral solution correspond to a single dose of 100 mg of the compound according to the invention.

Production:

The compound of the invention is suspended in the mixture of polyethylene glycol and polysorbate with stirring. The stirring process is continued until the compound according to the invention has completely dissolved.

i.v. Solution:

The compound of the invention is dissolved in a concentration below the saturation solubility in a physiologically tolerated solvent (e.g. isotonic saline solution, 5% glucose solution and/or 30% PEG 400 solution). The solution is sterilized by filtration and used to fill sterile and pyrogen-free injection containers.

The invention claimed is:
1. A compound of the formula (I)

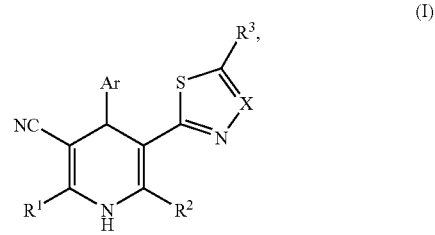

in which

Ar is $(C_6-C_{10})$-aryl which may be substituted once to three times, identically or differently, by substituents selected from the group consisting of halogen, cyano, $(C_1-C_4)$-alkyl, $(C_1-C_4)$-alkoxy and $(C_1-C_4)$-alkylthio, where said alkyl, alkoxy and alkylthio radicals may in turn be substituted by cyano or up to three times by fluorine, $R^1$ is $(C_1-C_6)$-alkyl which may be substituted by phenyl, or is $(C_1-C_6)$-alkylthio, where said alkyl and alkylthio radicals may in turn be substituted up to three times by fluorine, $R^2$ is $(C_1-C_6)$-alkyl which may be substituted by cyano, hydroxy, $(C_1-C_4)$-alkoxy, trifluoromethoxy, amino, mono-$(C_1-C_4)$-alkylamino, di-$(C_1-C_4)$-alkylamino, $(C_3-C_6)$-cycloalkyl, phenyl or up to three times by fluorine, or is $(C_3-C_6)$-cycloalkyl, X is C—$R^4$, and $R^3$ and $R^4$ are identical or different and independently of one another are hydrogen, halogen, amino, mono-$(C_1-C_4)$-alkylamino or di-$(C_1-C_4)$-alkylamino, are $(C_1-C_4)$-alkyl which may be substituted by hydroxy, $(C_1-C_4)$-alkoxy, amino, mono-$(C_1-C_4)$-alkylamino, di-$(C_1-C_4)$-alkylamino or up to three times by fluorine, or are phenyl which may be substituted by halogen, cyano, $(C_1-C_4)$-alkyl, trifluoromethyl, $(C_1-C_4)$-alkoxy or trifluoromethoxy, or a salt thereof.

2. A compound of the formula (I) as claimed in claim 1, in which

Ar is a group of the formula

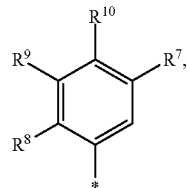

in which

* is the point of linkage to the dihydropyridine ring, $R^7$ is hydrogen or fluorine, $R^8$ is fluorine, chlorine, bromine, cyano or $(C_1-C_4)$-alkyl, $(C_1-C_4)$-alkoxy or $(C_1-C_4)$-alkylthio, each of which may be substituted up to three times by fluorine, $R^9$ is hydrogen, fluorine, chlorine or methyl, and $R^{10}$ is hydrogen, cyano, fluorine, chlorine or bromine, $R^1$ is $(C_1-C_4)$-alkyl which may be substituted up to three times by fluorine, $R^2$ is $(C_1-C_4)$-alkyl which may be substituted by $(C_1-C_4)$-alkoxy or up to three times by fluorine, X is C—$R^4$, and $R^3$ and $R^4$ are identical or different and independently of one another are hydrogen, fluorine, chlorine, amino, mono-$(C_1-C_4)$-alkylamino, di-$(C_1-C_4)$-alkylamino or $(C_1-C_4)$-alkyl, or a salt thereof.

3. A compound of the formula (I) as claimed in claim 1, in which

Ar is a group of the formula

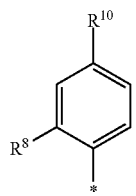

in which

* is the point of linkage to the dihydropyridine ring, $R^8$ is fluorine, chlorine, bromine, cyano, methyl, ethyl, trifluoromethyl, methoxy or trifluoromethoxy, and $R^{10}$ is fluorine, chlorine or cyano, $R^1$ is methyl or trifluoromethyl, $R^2$ is methyl, ethyl, n-propyl or methoxymethyl, X is C—$R^4$, $R^3$ is hydrogen, methyl or ethyl, $R^4$ is hydrogen, methyl, ethyl or n-propyl, or a salt thereof.

4. A process for preparing a compound of the formula (I) as defined in claim 1, comprising:

reacting a compound of the formula (II)

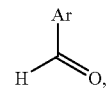

in which Ar has the meaning indicated in claim 1,

[A] in a one-stage process (one-pot reaction) with a compound of the formula (III)

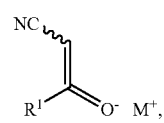

in which $R^1$ has the meaning indicated in claim 1 and $M^+$ is an alkali metal ion such as $Li^+$, $Na^+$ or $K^+$, and a compound of the formula (IV)

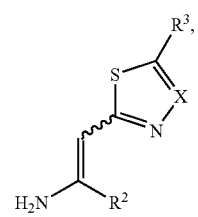

in which $R^2$, $R^3$ and X each have the meanings indicated in claim 1, or

[B] in a one-stage process (one-pot reaction) with a compound of the formula (V)

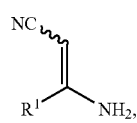

in which $R^1$ has the meanings indicated in claim 1, and a compound of the formula (VI)

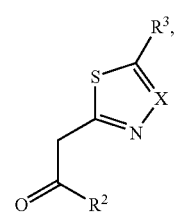

in which $R^2$, $R^3$ and X each have the meanings indicated in claim 1, or

[C] in a two-stage process comprising reacting the compound of formula (II) with a compound of the formula (VI) thereby producing a compound of the formula (VII)

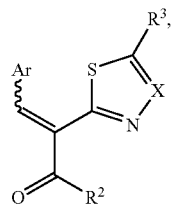

(VII)

in which Ar, $R^2$, $R^3$ and X each have the meanings indicated in claim 1, and reacting the compound of formula (VII) in a second step with a compound of the formula (V), and optionally reacting the resulting compound of formula (I) with the appropriate (i) solvents and/or (ii) bases or acids thereby producing a salt thereof.

5. A pharmaceutical composition comprising a compound of the formula (I) as defined in claim 1 and an inert, non-toxic, pharmaceutically suitable excipient.

* * * * *